(12) United States Patent
Zhang et al.

(10) Patent No.: US 10,383,830 B2
(45) Date of Patent: Aug. 20, 2019

(54) MODULATING ANTIBACTERIAL IMMUNITY VIA BACTERIAL MEMBRANE-COATED NANOPARTICLES

(71) Applicant: The Regents of the University of California, Oakland, CA (US)

(72) Inventors: Liangfang Zhang, San Diego, CA (US); Weiwei Gao, La Jolla, CA (US); Ronnie H. Fang, Irvine, CA (US); Che-Ming Jack Hu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/558,636

(22) PCT Filed: Mar. 18, 2016

(86) PCT No.: PCT/US2016/023077
§ 371 (c)(1),
(2) Date: Sep. 15, 2017

(87) PCT Pub. No.: WO2016/153979
PCT Pub. Date: Sep. 29, 2016

(65) Prior Publication Data
US 2018/0085320 A1    Mar. 29, 2018

Related U.S. Application Data

(60) Provisional application No. 62/136,035, filed on Mar. 20, 2015.

(51) Int. Cl.
| | | |
|---|---|---|
| *A61K 39/00* | (2006.01) | |
| *A61K 9/51* | (2006.01) | |
| *A61K 45/06* | (2006.01) | |
| *A61K 31/427* | (2006.01) | |
| *A61K 31/43* | (2006.01) | |
| *A61K 31/49* | (2006.01) | |
| *A61K 31/545* | (2006.01) | |
| *A61K 9/50* | (2006.01) | |
| *A61K 39/02* | (2006.01) | |
| *B82Y 5/00* | (2011.01) | |

(52) U.S. Cl.
CPC ......... *A61K 9/5176* (2013.01); *A61K 9/5068* (2013.01); *A61K 9/5192* (2013.01); *A61K 31/427* (2013.01); *A61K 31/43* (2013.01); *A61K 31/49* (2013.01); *A61K 31/545* (2013.01); *A61K 39/02* (2013.01); *A61K 45/06* (2013.01); *B82Y 5/00* (2013.01); *Y02A 50/401* (2018.01); *Y02A 50/478* (2018.01); *Y02A 50/48* (2018.01); *Y02A 50/484* (2018.01)

(58) Field of Classification Search
CPC .................................................. A61K 9/5176
See application file for complete search history.

(56) References Cited

U.S. PATENT DOCUMENTS

2013/0337066 A1    12/2013  Zhang et al.

OTHER PUBLICATIONS

PCT International Search Report and Written Opinion for PCT Application No. PCT/US2016/023077 dated Jun. 10, 2016 (8 pages).
McCaig et al., "Production of Outer Membrane Vesicles and Outer Membrane Tubes by Francisella Novicida," Journal of Bacteriology, 2013, 195(6):1120-1132.

*Primary Examiner* — Albert M Navarro
(74) *Attorney, Agent, or Firm* — Eversheds Sutherland (US) LLP

(57) ABSTRACT

Nanoparticles are provided comprising an inner core comprising a non-cellular material, and an outer surface comprising a bacterial membrane, e.g., a bacterial membrane derived from a bacteria outer membrane vesicle. Also provided are compositions, e.g., medicament delivery systems and pharmaceutical compositions, comprising the present nanoparticles. Also provided are uses of the present nanoparticles, pharmaceutical compositions and medicament delivery systems for treating and/or preventing a disease or condition, e.g., bacterial infection, in a subject.

16 Claims, 10 Drawing Sheets

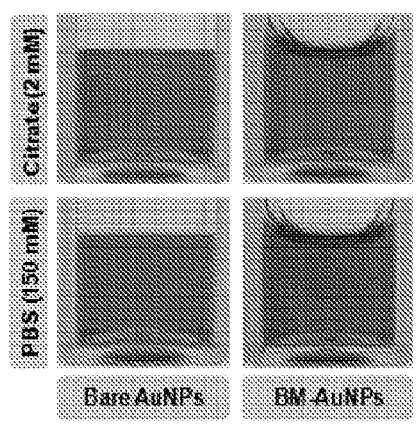 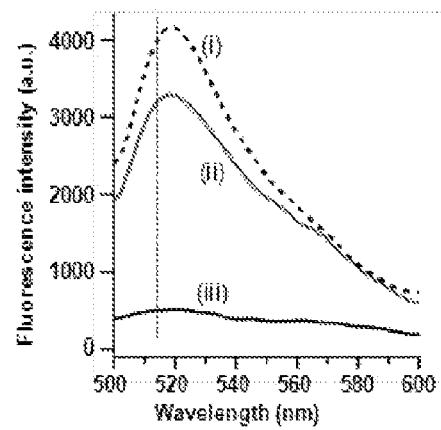
Figure 3A                                   Figure 3B

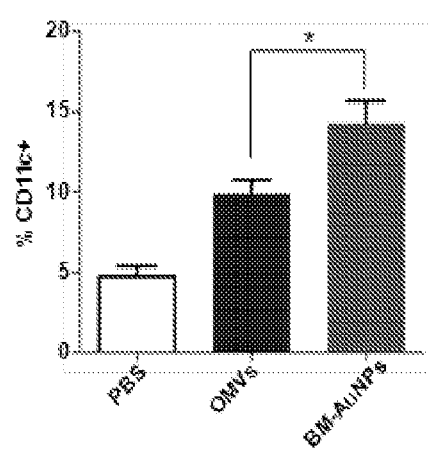
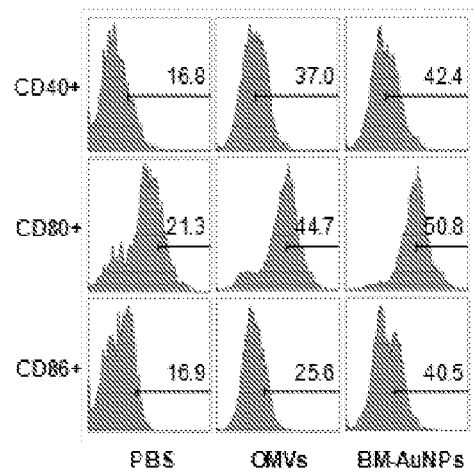
Figure 4A
Figure 4B
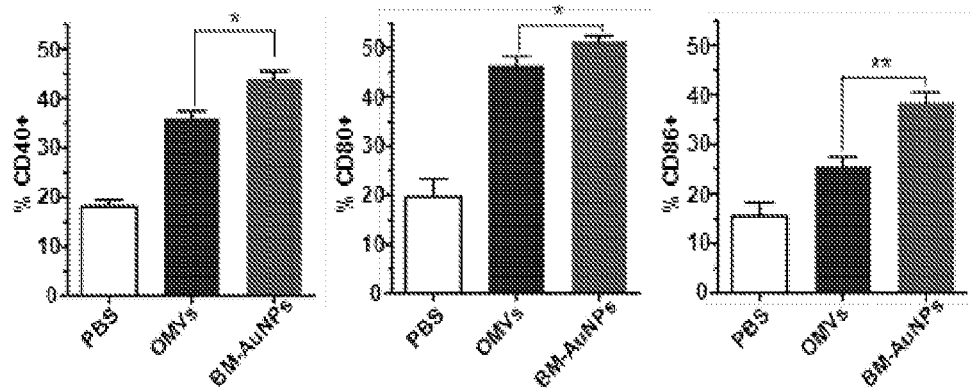
Figure 4C

MODULATING ANTIBACTERIAL IMMUNITY VIA BACTERIAL MEMBRANE-COATED NANOPARTICLES

CROSS REFERENCE TO RELATED APPLICATIONS

This application claims the priority benefit of PCT/US2016/023077 filed on Mar. 18, 2016 which claims priority benefit to U.S. Provisional Application Ser. No. 62/136,035, filed Mar. 20, 2015, entitled "Modulating Antibacterial Immunity via Bacterial Membrane-Coated Nanoparticles," the entire contents of which are hereby incorporated by reference herewith.

FIELD OF THE INVENTION

The present invention relates to nanoparticles comprising an inner core comprising a non-cellular material, and an outer surface comprising a bacterial membrane, e.g., a bacterial membrane derived from a bacteria outer membrane vesicle. The present invention also relates to compositions, e.g., medicament delivery systems and pharmaceutical compositions, comprising the present nanoparticles. The present invention further relates to the use of the present nanoparticles, pharmaceutical compositions and medicament delivery systems for treating and/or preventing a disease or condition, e.g., bacterial infection, in a subject.

BACKGROUND OF THE INVENTION

Despite the remarkable success in controlling former epidemics worldwide, vaccines effective against a number of serious infections, including those caused by pathogenic *Escherichia coli* (*E. coli*), *Helicobacter pylori*, and *Staphylococcus aureus*, remain largely unavailable.[1, 2] Meanwhile, existing antibiotic regimens are increasingly threatened by the rapid emergence of bacterial drug resistance.[3] Together, these challenges have motivated the search for novel antibacterial vaccine strategies.[4-6] Among various reported approaches, integrating synthetic nanoparticles with cues from natural immunity has shown tremendous promise.[7, 8] A plethora of nanoparticle-based vaccine systems have been developed to better manipulate immune responses and to potentially enhance antimicrobial immunity.[9]

On the front of nanotechnology development, combining synthetic nanoparticles with natural cellular materials has led to the creation of various biomimetic nanoparticles.[10, 11] In particular, using natural cellular membranes to cloak synthetic nanoparticles through a top-down fabrication method has recently attracted much attention.[12] The resulting cell membrane-coated nanoparticles preserve the highly tunable physicochemical properties of synthetic nanomaterials while harnessing complex cellular functions that are otherwise difficult to replicate. Based upon this new strategy, a variety of nanoparticle platforms mimicking natural cellular functions have been developed, including red blood cell (RBC) membrane-cloaked nanoparticles with long-circulating properties,[13] leukocyte membrane-coated silica microparticles capable of traversing endothelium,[14] and cancer cell membrane-coated nanoparticles with inherited homotypic cell binding as well as tumor-specific immune activation.[15] Cell membrane-coated nanoparticles have also enabled novel therapeutics beyond traditional practices. For example, by exploiting particle-bound RBC membranes, these biomimetic nanoparticles can function as a toxin nanosponge to absorb and neutralize a broad spectrum of pore-forming toxins regardless of the toxins' molecular structure.[16, 17] These toxin-sequestered nanoparticles can further present the undisrupted toxins to the immune system as a safe and effective toxin vaccine.[16, 17]

SUMMARY OF THE INVENTION

In one aspect, the present invention provides for a nanoparticle comprising: a) an inner core comprising a non-cellular material; and b) an outer surface comprising a bacterial membrane. In some embodiments, the bacterial membrane is a modified or processed bacterial membrane, or the bacterial membrane is derived from a bacteria outer membrane vesicle, or the nanoparticle is configured as a vaccine. Medicament delivery systems and pharmaceutical compositions comprising the present nanoparticles are also provided. Methods using the present nanoparticles, pharmaceutical compositions and medicament delivery systems for treating and/or preventing a disease or condition in a subject are further provided. The present invention is further directed to use of an effective amount of present nanoparticles for the manufacture of a medicament for treating and/or preventing a disease or condition in a subject.

In another aspect, the present invention provides for a bacterial specific immunogenic composition, which immunogenic composition comprises an effective amount of the present nanoparticles. Vaccines that comprise the present immunogenic compositions are also provided. Methods using the present immunogenic compositions or vaccines for treating and/or preventing bacterial infection in a subject are further provided.

In still another aspect, the present invention provides for a process for making a nanoparticle, which process comprises mixing a nanoparticle inner core comprising a non-cellular material with a bacterial membrane while exerting exogenous energy to form a nanoparticle comprising said inner core and an outer surface comprising said bacterial membrane. Nanoparticles made by the present processes are also provided. Use of an effective amount of nanoparticles made by the present processes for the manufacture of a medicament for treating and/or preventing a disease or condition in a subject is further provided. In some embodiments, the bacterial membrane is a modified or processed bacterial membrane, or the bacterial membrane is derived from a bacteria outer membrane vesicle, or the nanoparticle is configured as a vaccine.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

BRIEF DESCRIPTION OF THE DRAWINGS

FIG. 2A is the Hydrodynamic sizes (diameter, nm) and FIG. 2B is the surface zeta potentials (mV) of AuNPs before coating and after coating, in comparison with those of OMVs. FIG. 2C is a representative TEM image showing the spherical core-shell structure of the BM-AuNPs negatively stained with uranyl acetate (scale bar, 50 nm). Inset: a zoomed-in view of a single BM-AuNP (scale bar, 10 nm). FIG. 2D is the quantification of protein concentration of AuNPs before and after the membrane coating by using a BCA assay. Protein loading yield is defined as the weight ratio of immobilized proteins to the gold nanoparticles.

FIGS. 3A-3B illustrate the stability and membrane-core affinity of BM-AuNP. FIG. 3A is Both bare AuNPs and BM-AuNPs are stable in 2 mM citrate storage buffer. However, in 1×PBS, bare AuNPs rapidly aggregate while BM-AuNPs remain stable. FIG. 3B is a fluorescence quenching assay shows the strong affinity between the coated bacterial membrane and the gold cores. Fluorescence spectra were taken from i) FITC-thiol alone, ii) FITC-thiol mixed with BM-AuNPs, and iii) FITC-thiol mixed with bare AuNPs. The concentrations of FITC-thiol and AuNP are 1 nM and 0.025 nM (equivalent to 50 µg mL$^{-1}$), respectively.

FIGS. 4A-4C illustrate BM-AuNPs activating DCs in the draining lymph nodes in vivo. FIG. 4A is the percentage CD11c+ cells in a total of 20,000 lymphocytes from naive mice or mice vaccinated with either OMVs or BM-AuNPs (2.5 µg gold) 12 h after the subcutaneous injection. Data are shown with mean frequencies±SEM (standard error of the mean) measured per lymph node (*p<0.05). FIG. 4B is a representative flow cytometry analysis of surface maturation markers (CD40, CD80, and CD86) on CD11c+ DCs from lumbar and sacral lymph nodes of the mice (n=5). FIG. 4C is the quantification of the pencentage of CD11c+ DCs based on the histograms in (b). Data are shown with mean percentage±SEM (*p<0.05, **p<0.01). Three independent experiments were carried out.

FIG. 5A is the Anti-*E. coli* IgG titres at day 21 (n=6). Black lines indicate geometric means. Naive mice were monitored as a negative control (open circles). FIG. 5B is the time course of anti-*E. coli* IgG titres in naive mice (open circles) and mice immunized with 0.2 µg antigen/dose BM-AuNPs (red squares), 0.2 µg antigen/dose OMVs (blue squares), 0.02 µg antigen/dose BM-AuNPs (red triangles), and 0.02 µg antigen/dose OMVs (blue triangles), respectively (n=6). FIG. 5C is the quantified avidity index of the anti-sera from immunized mice (0.2 µg antigen/dose) binding to *E. coli* bacteria (n=6). *p<0.05, **p<0.01.

FIG. 9A—The lymph node from mice injected with 30 nm BM-AuNPs showed dark grey. FIG. 9B—The lymph node from mice injected with 90 nm BM-AuNPs showed an opulent color of natural tissue, suggesting a lower level of gold accumulation. FIG. 9C—Gold concentration was quantified by using ICP-MS and compared between mice injected with 30 and 90 nm BM-AuNP, respectively.

DETAILED DESCRIPTION OF THE INVENTION

Figure 1:
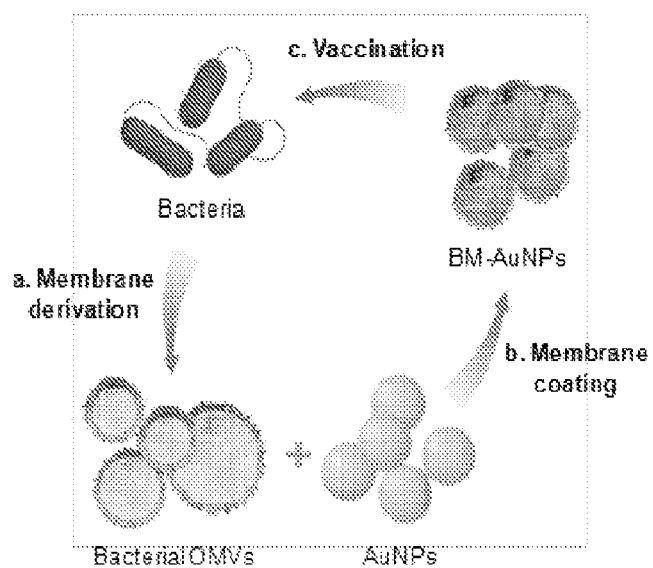
FIG. 1 is a schematic illustration of modulating antibacterial immunity via bacterial membrane-coated nanoparticles. Briefly, bacterial membrane was first collected from source bacteria in the form of secreted outer membrane vesicles (OMVs) and then mixed with citrate-stabilized gold nanoparticles (AuNPs) with a diameter of approximately 30 nm. Through an extrusion process, OMVs were fused with AuNPs, translocating the entire bacterial membrane onto gold surfaces to form bacterial membrane-coated AuNPs (BM-AuNPs). When injected subcutaneously into mice, BM-AuNPs elicited bacterium-specific immunity against the source bacteria.

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual*, 2$^{nd}$ ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and *Remington, The Science and Practice of Pharmacy*, 20$^{th}$ ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Nanoparticles and Uses Thereof

In one aspect, the present invention provides for a nanoparticle comprising: a) an inner core comprising a noncellular material; and b) an outer surface comprising a bacterial membrane, e.g., plasma membrane. In some embodiments, the bacterial membrane is a modified or processed bacterial membrane, or the bacterial membrane is derived from a bacteria outer membrane vesicle, or the nanoparticle is configured as a vaccine.

The present nanoparticle can comprise any suitable inner core. For example, the inner core of the present nanoparticle can comprise an inorganic substance, an organic substance, or an aggregate or a complex thereof. In another example, the inner core of the present nanoparticle can comprise a polymeric particle core, a silica particle core, or a metal, e.g., gold, particle core. In some embodiments, the inner core, e.g., the polymeric particle core, can comprise an optical shift property. In other embodiments, the inner core, e.g., the polymeric particle core, can comprise a metal, e.g., gold, iron oxide or a quantum dot. In still other embodiments, the inner core of the nanoparticle can comprise a biocompatible, a synthetic material or a polymer, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the present nanoparticle supports the outer surface.

The outer surface of the present nanoparticle can comprise any suitable modified or processed bacterial membrane. For example, the bacterial membrane can be modified or processed via any suitable physical, chemical or biological methods. In some embodiments, the bacterial membrane can be treated with enzyme(s), e.g., protease(s), to remove proteins or peptides on the bacterial membrane or bacterial plasma membrane.

In some embodiments, the nanoparticle can be configured as a vaccine, e.g., a bacterial specific vaccine. Preferably, the nanoparticle can be configured as a vaccine against a bacterium that is the same bacterial species from which the bacterial membrane in the nanoparticle is derived. Also preferably, the vaccine further comprises an immunogenic adjuvant and/or potentiator.

The outer surface of the present nanoparticle can comprise any suitable bacterial membrane, e.g., bacterial membrane derived from a bacteria outer membrane vesicle. For example, the outer surface can comprise a membrane derived from a gram-positive bacterium, e.g., a membrane derived from an outer membrane vesicle of a gram-positive bacterium that possesses an outer cell membrane, such as a membrane derived from an outer membrane vesicle of *Deinococcus*.

In another example, the outer surface can comprise a membrane derived from a gram-negative bacterium or a diderm bacterium, e.g., a membrane derived from an outer membrane vesicle of a gram-negative bacterium or a diderm bacterium. The outer surface can comprise a membrane derived from an outer membrane vesicle of any suitable diderm bacterium. Exemplary diderm bacterium can be a simple diderm bacterium lacking lipopolysaccharide, an archetypical diderm bacterium, in which the outer cell membrane contains lipopolysaccharide, or a diderm bacterium, in which outer cell membrane is made up of mycolic acid.

The outer surface can comprise a membrane derived from a gram-negative bacterium, e.g., a membrane derived from an outer membrane vesicle of any suitable gram-negative bacterium. Exemplary gram-negative bacterium can be a bacterium in a genus of proteobacteria, aquificae, chlamydiae, bacteroidetes, green sulfur bacteria, cyanobacteria, fibrobacteres, verrucomicrobia, planctomycetes, spirochaetes, or acidobacteria. The bacterium in a genus of proteobacteria can be an *Escherichia*, a *Salmonella*, a *Vibrio*, a *Helicobacter*, or a *Yersinia*. The bacterium in a genus of chlamydiae can be *Chlamydia trachomatis*, *Chlamydophila pneumoniae* or *Chlamydophila psittaci*. The bacterium in a genus of green sulfur bacteria can be *Chlorobium tepidum*. The bacterium in a genus of spirochaetes can be a *Leptospira* species, *Borrelia burgdorferi*, *B. garinii*, *B. afzelii*, *Borrelia recurrentis*, *Treponema pallidum*, *Brachyspira pilosicoli* or *Brachyspira aalborgi*.

In some embodiments, the outer surface can comprise a membrane derived from a plasma membrane or an outer membrane vesicle of *Escherichia coli* (*E. coli*), *Salmonella*, *Shigella*, *Enterobacteriaceae*, *Pseudomonas*, *Moraxella catarrhalis*, *Helicobacter*, *Stenotrophomonas*, *Bdellovibrio*, acetic acid bacteria, or *Legionella*. In other embodiments, the outer surface can comprise a membrane derived from a plasma membrane or an outer membrane vesicle of a medically relevant gram-negative cocci, such as an organism that causes a sexually transmitted disease (e.g., *Neisseria gonorrhoeae*), a meningitis (e.g., *Neisseria meningitidis*), or respiratory symptoms (e.g., *Moraxella catarrhalis* or *Haemophilus Influenzae*). In still other embodiments, the outer surface can comprise a membrane derived from a plasma membrane or an outer membrane vesicle of a medically relevant gram-negative bacilli, such as an organism that causes primarily respiratory problems (e.g., *Klebsiella pneumoniae, Legionella pneumophila*, or *Pseudomonas aeruginosa*), primarily urinary problems (e.g., *Escherichia coli, Proteus mirabilis, Enterobacter cloacae,* or *Serratia marcescens*), or primarily gastrointestinal problems (e.g., *Helicobacter pylori, Salmonella enteritidis,* or *Salmonella typhi*). In yet other embodiments, the outer surface can comprise a membrane derived from a plasma membrane or an outer membrane vesicle of a gram-negative bacterium that is associated with a hospital-acquired infection (HAI). Such gram-negative bacterium can cause bacteremia, secondary meningitis, and/or ventilator-associated pneumonia, e.g., in hospital intensive-care units. For example, such gram-negative bacterium can be *Acinetobacter baumannii*.

The cellular membrane of the present nanoparticle can comprise membrane-bound proteins, glycans and/or a complex lipopolysaccharide (LPS), e.g., LPS comprising or consisting of lipid A, core polysaccharide, and O antigen. In some embodiments, the lipid portion of the complex lipopolysaccharide (LPS) can act as an endotoxin. In other embodiments, the lipid portion of the LPS can be removed or the level of the lipid portion of the LPS can be reduced.

The present nanoparticle can have any suitable size. For example, the present nanoparticle can have a diameter from about 10 nm to about 10 µm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm, or any sub-range within about 10 nm to about 10 µm, e.g., any range between any two of the above sizes. In some embodiments, the present nanoparticle can have a diameter from about 30 nm to about 60 nm, e.g., about 30-40 nm, 30-50 nm, 40-50 nm, 40-60 nm or 50-60 nm.

The present nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the present nanoparticle can substantially lack constituents of the bacterial cell or bacteria outer membrane vesicle from which the cellular membrane is derived. For example, the present nanoparticle can lack at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the bacterial cell or bacteria outer membrane vesicle from which the cellular membrane is derived. The present nanoparticle can lack any constituents of the bacterial cell or bacteria outer membrane vesicle from which the cellular membrane is derived. For example, the present nanoparticle can lack bacterial cell signaling biochemicals, bacterial DNA, RNA, proteins, endotoxins, and/or allied virulence molecules.

In some embodiments, the present nanoparticle can substantially maintain natural structural integrity or activity of the cellular membrane or the constituents of the cellular membrane derived from a bacterial cell or a bacteria outer membrane vesicle. For example, the present nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity or activity for eliciting a bacteria specific immune response in a subject.

In some embodiments, the present nanoparticle can be biocompatible or biodegradable. For example, the inner core of the present nanoparticle can comprise PLGA and the outer surface of the nanoparticle can comprise a bacterial membrane, e.g., a bacterial membrane derived from a bacteria outer membrane vesicle.

The outer surface of the present nanoparticle can further comprise a synthetic membrane. In some embodiments, the present nanoparticles comprise a mixture of nanoparticles that comprise an outer surface comprising a bacterial membrane and nanoparticles that comprise an outer surface comprising a synthetic membrane. The nanoparticles that comprise an outer surface comprising a synthetic membrane may or may not be capable of eliciting a bacteria specific immune response in a subject. In some embodiments, both the nanoparticles that comprise an outer surface comprising a bacterial membrane and nanoparticles that comprise an outer surface comprising a synthetic membrane are capable of eliciting a bacteria specific immune response in a subject. In other embodiments, the nanoparticles that comprise an outer surface comprising a bacterial membrane is capable of eliciting a bacteria specific immune response in a subject, but the nanoparticles that comprise an outer surface comprising a synthetic membrane is not capable of eliciting a bacteria specific immune response in a subject.

The present nanoparticles can comprise the nanoparticles that comprise an outer surface comprising a bacterial membrane and nanoparticles that comprise an outer surface comprising a synthetic membrane in any suitable ratio. In some embodiments, The present nanoparticles can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a bacterial membrane. In other embodiments, the present nanoparticles can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the present nanoparticles can comprise about 1-10% (w/w) of the nanoparticles that comprise an outer surface comprising a bacterial membrane and about 90-99% (w/w) of the nanoparticles that comprise an outer surface comprising a synthetic membrane, about 11-25% (w/w) of the nanoparticles that comprise an outer surface comprising a bacterial membrane and about 75-89% (w/w) of the nanoparticles that comprise an outer surface comprising a synthetic membrane, about 50% (w/w) of the nanoparticles that comprise an outer surface comprising a bacterial membrane and about 50% (w/w) of the nanoparticles that comprise an outer surface comprising a synthetic membrane, about 51-75% (w/w) of the nanoparticles that comprise an outer surface comprising a bacterial membrane and about 49-25% (w/w) of the nanoparticles that comprise an outer surface comprising a synthetic membrane, or about 90-100% (w/w) of the nanoparticles that comprise an outer surface comprising a bacterial membrane and about 0-10% (w/w) of the nanoparticles that comprise an outer surface comprising a synthetic membrane.

The outer surface of the present nanoparticle can comprise a hybrid membrane comprising a cellular membrane derived from a bacterium and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane derived from a bacterium. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane derived from a bacterium and about 95-99%

(w/w) of a synthetic membrane, about 11-25% (w/w) of a cellular membrane derived from a bacterium and about 75-89% (w/w) of a synthetic membrane, about 50% (w/w) of a cellular membrane derived from a bacterium and about 50% (w/w) of a synthetic membrane, about 51-75% (w/w) of a cellular membrane derived from a bacterium and about 49-25% (w/w) of a synthetic membrane, or about 90-99% (w/w) of a cellular membrane derived from a bacterium and about 1-10% (w/w) of a synthetic membrane.

The present nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle.

The releasable cargo can comprise any suitable substance or agent, e.g., a therapeutic agent, a prophylactic agent, a diagnostic or marker agent, a prognostic agent, an isolation agent, a monitoring agent, or a combination thereof. The therapeutic agent or prophylactic agent can be any suitable substance or agent, e.g., an anti-viral agent, an antibiotic, an anti-fungal agent, or an anti-protozoa agent. In some embodiments, the therapeutic agent or prophylactic agent is quinine.

In some embodiments, the therapeutic agent or prophylactic agent is an antibiotic. Any suitable antibiotic can be used. For example, the antibiotic can have a bactericidal activity or bacteriostatic activity. In another example, the antibiotic can be a narrow-spectrum or a broad-spectrum antibiotic. In still another example, the antibiotic can target the bacterial cell wall (e.g., penicillins and cephalosporins), can target the cell membrane (e.g., polymyxins), can interfere with essential bacterial enzymes (e.g., rifamycins, lipiarmycins, quinolones and sulfonamides), targets protein synthesis (e.g., macrolides, lincosamides and tetracyclines), or can be a cyclic lipopeptide (such as daptomycin), a glycylcycline (such as tigecycline), an oxazolidinone (such as linezolid), or a lipiarmycin (such as fidaxomicin).

In other embodiments, the antibiotic can be an inhibitor of cell wall synthesis, an inhibitor of protein synthesis, an inhibitor of membrane function, an inhibitor for folate pathway, or an inhibitor of nucleic acid synthesis function. Any suitable inhibitor of cell wall synthesis can be used. For example, the inhibitor of cell wall synthesis can be penicillin, cephalosporin, monobactam, penem, a glycopeptide, or a lipoglycopeptide.

In some embodiments, the present nanoparticle can further comprise exemplary antibiotic(s), or a combination thereof, listed in the following Table 1.

TABLE 1

| Exemplary Antibiotics | |
|---|---|
| | International Common Name Examples |
| Beta-lactams (Penicillins)- Inhibitors of Cell Wall Synthesis | |
| Penicillins (pen G) | Penicillin G |
| Penicillinase-stable penicillins (pen M) | Oxacillin |
| | Methicillin |
| Aminopenicillins (pen A) | Ampicillin |
| Penicillinase labile: hydrolyzed by staphylococcal penicillinase | Amoxicillin |
| Carboxypenicillins (pen C) | Ticarcillin |
| Ureidopenicillins (pen U) | Piperacillin |
| Beta-lactam/Beta-lactamase inhibitor combinations | Amoxicillin + clavulanic acid |
| | Ampicillin + sulbactam |
| | Ticarcillin + clavulanic acid |
| | Piperacillin + tazobactam |
| Amidinopenicillin | Mecillinam |
| Beta-lactams (Cephems)-Inhibitors of Cell Wall Synthesis | |
| 1st Generation Cephalosporins C1G | Cephalothin |
| | Cefazolin |
| 2nd Generation Cephalosporins C2G | Cefuroxime |
| | Cefamandole |
| | Cephamycin (new C2G) |
| | Cefoxitin |
| | Cefotetan - |
| 3rd Generation Cephalosporins C3G | Cefotaxime |
| | Ceftazidime |
| | Ceftriaxone |
| 4th Generation Cephalosporins C4G Oral C3G | Cefepime |
| Next Generation Cephalosporins (Anti-MRSA) | Ceftobiprole |
| | Ceftaroline |
| Beta-lactams-Inhibitors of Cell Wall Synthesis | |
| Monobactams | Aztreonam |
| Penems | Imipenem |
| Carbapenems | Meropenem |
| Penems | Etrapenem |
| | Doripenem |
| | Faropenem |
| Glycopeptides - Inhibitors of Cell Wall Synthesis | |
| Glycopeptides | Vancomycin |
| Lipoglycopeptides | Dalbavancin |
| | Oritavancin |
| | Teavanacin |
| | Teicoplanin |
| Inhibitors of Protein Synthesis | |
| Aminoglycosides - (Bactericidal) | Gentamicin |
| | Streptomycin |
| | Tobramycin |
| | Kanamycin |
| | Amikacin |
| Macrolide-lincosamide-streptogramin-ketolide- (MLSK) (Bacteriostatic) | Erythromycin |
| | Clindamycin |
| | Quinupristin-Dalfopristin (Synercid) |
| | Clarithromycin |
| | Azithromycin |
| | Telithromycin |
| Tetracyclines-(Bacteriostatic) | Tetracycline |
| | Doxycycline |
| | Minocycline |
| Glycylcyclines | Tigecycline |
| Phenocols (Bacteriostatic) | Chloramphenicol |
| Oxazolidinones (Bactericidal for Streptococci; Bacteriostatic for Enterococcus and Staphylococci) | Linezolid |
| Ansamycins ((Bacteriostatic or Bactericidal depending on organism and concentration) | Rifampin |
| Inhibitors of Membrane Function | |
| Lipopeptides | Polymyxin B |
| | Colistin |

TABLE 1-continued

Exemplary Antibiotics

| | International Common Name Examples |
|---|---|
| Cyclic Lipopeptides | Daptomycin |
| Antimetabolites- Folate Pathway Inhibitors | |
| Sulfonamides (Bactericidal)- Inhibits pteridine synthase and dihydrofolic acid reductase | Trimethoprim/ Sulfamethoxazole |
| Inhibitors of Nucleic Acid Synthesis Function | |
| Fluoroquinolones (Bactericidal)- Inhibits DNA Gyrase and Topoisomerase | Ciprofloxacin Levofloxacin Gatifloxacin Moxifloxacin Garenoxacin Lomefloxacin Norfloxacin Sparfloxacin |
| Quinolones First Generation- Narrow spectrum (Only gram negatives) | Nalidixic Acid Cinoxacin |
| Furanes (Bactericidal)- Gram positive and gram negative urinary tract infections | Nitrofurantoin |

(Adapted from Biomerieux Vitek 2 Customer Education March 2008-<http://www.biomerieux-usa.com/upload/VITEK-Bus-Module-1-Antibiotic-Classification-and-Modes-of-Action-1.pdf>).

In some embodiments, the bacterial membrane in the outer surface of the present nanoparticle has a protein loading yield, defined as the weight ratio of immobilized proteins to the nanoparticle, of at least from about 1 wt % to about 95 wt %, or more, e.g., at least about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 30 wt %, 40 wt %, 50 wt %, 60 wt %, 70 wt %, 80 wt %, 90 wt %, 95 wt %, or more.

In some embodiments, the present nanoparticle is substantially stable, e.g., not aggregating, in a biological or physiological solution or environment, e.g., biological buffer or in vivo environment. For example, at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the present nanoparticles do not aggregate in a biological or physiological solution or environment, e.g., biological buffer or in vivo environment, for at least 1 minute, 2 minutes, 3 minutes, 4 minutes, 5 minutes, 6 minutes, 7 minutes, 8 minutes, 9 minutes, 10 minute, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 16 hours, 1 day, 2 days, 3 days, 4 days, 5 days, 6 days, 1 week or longer.

In some embodiments, the present nanoparticle substantially maintains its size in a biological or physiological solution or environment, e.g., biological buffer or in vivo environment. For example, at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the present nanoparticles maintain their sizes in a biological or physiological solution or environment, e.g., biological buffer or in vivo environment, for at least 1 hour, 2 hours, 3 hours, 4 hours, 5 hours, 6 hours, 7 hours, 8 hours, 9 hours, 10 hours, 16 hours, 1 day, 2 days, 3 days, 4 days, 5 days, 6 days, 1 week or longer.

In some embodiments, the outer surface of the present nanoparticle substantially shields inner core. For example, the outer surface of the present nanoparticle shields at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the inner core.

In some embodiments, the outer surface of the present nanoparticle is configured not to be substantially replaced by a reactive agent, e.g., a thiol containing agent. For example, at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the outer surface of the present nanoparticle is configured not to be substantially replaced by a reactive agent, e.g., a thiol containing agent.

In some embodiments, the present nanoparticle is configured to elicit an immune response to the constituents of the bacterial membrane, the bacterial membrane, or the bacterium from which the bacterial membrane in the outer surface is derived from.

In some embodiments, the present nanoparticle is configured to activate a dendritic cell (DC), e.g., activating a dendritic cell in vivo. The present nanoparticle can also be configured to enhance DC maturation level in vivo.

In some embodiments, the present nanoparticle is configured to elicit a humoral immune response to the constituents of the bacterial membrane, the bacterial membrane or the bacterium from which the bacterial membrane in the outer surface is derived from. The present nanoparticle can also be configured to generate an antibody having a higher avidity than that of an antibody generated by a comparable bacteria outer membrane vesicle.

In some embodiments, the present nanoparticle is configured to elicit a cellular immune response, e.g., T cell response, to the constituents of the bacterial membrane, the bacterial membrane or the bacterium from which the bacterial membrane in the outer surface is derived from. For example, the present nanoparticle can be configured to elicit a stronger cellular immune response than that generated by a comparable bacteria outer membrane vesicle. For example, the present nanoparticle can also be configured to induce or enhance expression of a cytokine associated with T cell activation. The exemplary cytokines include interferon gamma (IFNγ), interleukin 17 (IL-17) and interleukin 4 (IL-4).

In some embodiments, the bacterial membrane, e.g., the bacterial membrane derived from a bacteria outer membrane vesicle, of the present nanoparticle comprises a modification. The modification can be made by any suitable ways. For example, the modification can be made by physical, chemical and/or biological methods. In some embodiments, the modification can be made by genetic engineering or enzymatic treatment(s), protease treatment(s). The bacterial membrane of the present nanoparticle can be modified to comprise any suitable substance. For example, the bacterial membrane can be modified to comprise a mutant or an exogenous antigen.

In some embodiments, the present disclosure provides for a medicament delivery system, which comprises an effective amount of the present nanoparticle. The medicament delivery system can further comprise another active ingredient, and/or a medically and/or pharmaceutically acceptable carrier or excipient.

In some embodiments, the present disclosure provides for a pharmaceutical composition, which pharmaceutical composition comprises an effective amount of the present nanoparticle and a pharmaceutically acceptable carrier or excipient. The pharmaceutical composition can further comprise another active ingredient, e.g., an antibiotic.

The present disclosure provides for a method for treating and/or preventing a disease or condition in a subject, which method comprises administering, to a subject in need of such treatment and/or prevention, an effective amount of the present nanoparticle, the present medicament delivery system, or the present pharmaceutical composition. The present method can be used to treat and/or prevent any suitable disease or condition in a subject. In some embodiments, the disease or condition is bacterial infection. The present method can be used to treat and/or prevent infection by a gram-positive bacterium or a gram-negative bacterium. In some embodiments, the bacterium can be in a genus of *Staphylococcus, Escherichia, Streptococcus* or *Helicobacter*. For example, the bacterium can be in the genus of *Staphylococcus*. The *Staphylococcus* bacterium can be in *S. aureus* group (e.g., *S. aureus* or *S. simiae*), *S. auricularis* group (e.g., *S. auricularis*), *S. carnosus* group (e.g., *S. carnosus, S. condimenti, S. massiliensis, S. piscifermentans,* or *S. simulans*), *S. epidermidis* group (e.g., *S. capitis, S. caprae, S. epidermidis,* or *S. saccharolyticus*), *S. haemolyticus* group (e.g., *S. devriesei, S. haemolyticus,* or *S. hominis*), *S. hyicus-intermedius* group (e.g., *S. chromogens, S. felis, S. delphini, S. hyicus, S. intermedius, S. lutrae, S. microti, S. muscae, S. pseudintermedius, S. rostri,* or *S. schleiferi*), *S. lugdunensis* group (e.g., *S. lugdunensis*), *S. saprophyticus* group (e.g., *S. arlettae, S. cohnii, S. equorum, S. gallinarum, S. kloosii, S. leei, S. nepalensis, S. saprophyticus, S. succinus,* or *S. xylosus*), *S. sciuri* group (e.g., *S. fleurettii, S. lentus, S. sciuri, S. stepanovicii,* or *S. vitulinus*), *S. simulans* group (e.g., *S. simulans*) or *S. warneri* group (e.g., *S. pasteuri,* or *S. warneri*). In another example, the bacterium can be in the genus of *Escherichia,* e.g., *Escherichia coli*. In still another example, the bacterium can be in the genus of *Streptococcus*. The *Streptococcus* bacterium can be *Streptococcus pyogenes, Streptococcus agalactiae, Streptococcus equisimilis, Streptococcus bovis, Streptococcus anginosus, Streptococcus sanguinis, Streptococcus suis, Streptococcus mitis, Streptococcus mutans,* or *Streptococcus pneumoniae*. In yet another example, the bacterium can be in the genus of *Helicobacter*. The *Helicobacter* bacterium can be *Helicobacter pylori* or a non-*pylori Helicobacter* species. The non-*pylori Helicobacter* species can be *H. suis, H. baculiformis, H. equorum, H. hepaticus, H. mustelae, H. bilis, H. felis, H. bizzozeronii, H. salomonis, H. ganmani, H. pullorum, H. anseris, H. brantae, H. cinaedi* or *H. canis*. Preferably, the present method can be used to treat and/or prevent bacterial infection of a bacterium that is the same bacterial species from which the bacterial membrane in the nanoparticle is derived.

The present method can be used to treat and/or prevent a disease or condition in any suitable subject. For example, the present method can be used to treat and/or prevent a disease or condition in a human or a non-human mammal. The present method can further comprise administering another active ingredient to the subject and/or a pharmaceutically acceptable carrier or excipient to the subject. The present nanoparticle can also be administered via a medicament delivery system. The present nanoparticle, medicament delivery system and/or pharmaceutical composition can be administered via any suitable route. For example, the present nanoparticle, medicament delivery system and/or pharmaceutical composition can be administered via an oral, nasal, inhalational, parental, intravenous, intraperitoneal, subcutaneous, intramuscular, intradermal, topical, or rectal route.

In another aspect, the present invention is directed to use of an effective amount of the present nanoparticle for the manufacture of a medicament for treating and/or preventing a disease or condition in a subject.

The present disclosure also provides for a bacterial specific immunogenic composition, which immunogenic composition comprises an effective amount of the present nanoparticle. The present immunogenic composition can further comprise an immunogenic adjuvant and/or potentiator. The present disclosure further provides for a vaccine, which comprises present immunogenic composition. The present vaccine can further comprise an immunogenic adjuvant and/or potentiator.

The present disclosure further provides for a method for treating and/or preventing bacterial infection in a subject, which method comprises administering, to a subject in need of such treatment and/or prevention, an effective amount of the present immunogenic composition or the present vaccine. The present method can be used to treat and/or prevent any suitable bacterial infection in a subject. Preferably, the present method can be used to treat and/or prevent bacterial infection of a bacterium that is the same bacterial species from which the bacterial membrane in the nanoparticle is derived.

The present method can be used to treat and/or prevent a disease or condition in any suitable subject. For example, the present method can be used to treat and/or prevent a disease or condition in a human or a non-human mammal. The present method can further comprise administering another active ingredient, e.g., an antibiotic, to the subject and/or a pharmaceutically acceptable carrier or excipient to the subject. The present nanoparticle can also be administered via a medicament delivery system. The present nanoparticle, medicament delivery system and/or pharmaceutical composition can be administered via any suitable route. For example, the present nanoparticle, medicament delivery system and/or pharmaceutical composition can be administered via an oral, nasal, inhalational, parental, intravenous, intraperitoneal, subcutaneous, intramuscular, intradermal, topical, or rectal route.

In some embodiments, the present methods are used to treat bacterial infection in a subject. In other embodiments, the present methods are used to prevent bacterial infection in a subject or to protect a subject from bacterial infection.

B. Processes for Making a Nanoparticle

In still another aspect, the present invention provides for a process for making a nanoparticle, which process comprises mixing a nanoparticle inner core comprising a non-cellular material with a bacterial membrane, e.g., a bacterial membrane derived from a bacteria outer membrane vesicle, while exerting exogenous energy to form a nanoparticle comprising said inner core and an outer surface comprising said bacterial membrane, e.g., a bacterial membrane derived from a bacteria outer membrane vesicle.

Any suitable exogenous energy can be used. For example, the exogenous energy can be a mechanical energy, an acoustic energy and/or a thermal energy. In some embodiments, the mechanical energy can be exerted by extrusion. In some embodiments, the acoustic energy can be exerted by sonication. In some embodiments, the thermal energy can be exerted by heating.

The bacteria outer membrane vesicle can be prepared by any suitable methods. For example, the bacteria outer membrane vesicle can be prepared by removing bacterial cells and collecting the bacteria outer membrane vesicle from a bacterial culture liquid. The bacterial cells can be removed by any suitable methods. In some embodiments, the bacterial cells can be removed by filtration or a low-speed centrifugation, e.g., centrifugation conducted at about 3,000×g to about 8,000×g. For example, the centrifugation can be conducted at about 3,000×g, 4,000×g, 5,000×g, 6,000×g, 7,000×g, or 8,000×g.

The present process can further comprise concentrating the bacteria outer membrane vesicle. The bacteria outer membrane vesicle can be concentrated by any suitable methods. For example, the bacteria outer membrane vesicle can be concentrated by filtration.

The bacteria outer membrane vesicle can be collected by any suitable methods. In some embodiments, the bacteria outer membrane vesicle can be collected by a high-speed centrifugation, e.g., high-speed centrifugation conducted at about 10,000×g to about 300,000×g. For example, the centrifugation can be conducted at about 10,000×g, 50,000×g, 100,000×g, 110,000×g, 120,000×g, 130,000×g, 140,000×g, 150,000×g, 160,000×g, 170,000×g, 180,000×g, 190,000×g, 200,000×g, 210,000×g, 220,000×g, 230,000×g, 240,000×g, 250,000×g, 260,000×g, 270,000×g, 280,000×g, 290,000×g, or 300,000×g.

Nanoparticles made by the present process are also provided. The nanoparticles made by the present process can be used for any suitable purpose. For example, an effective amount of the nanoparticles made by the present process can be used for the manufacture of a medicament for treating and/or preventing a disease or condition, e.g., bacterial infection, in a subject.

In some embodiments, the bacterial membrane is a modified or processed bacterial membrane, or the bacterial membrane is derived from a bacteria outer membrane vesicle, or the nanoparticle is configured as a vaccine.

D. Pharmaceutical Compositions and Administration Routes

The pharmaceutical compositions comprising the present nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, or 1%. In certain embodiments, methylcellulose is in a suspension of about 0.5%.

E. Exemplary Embodiments

Compositions of Matter and Methods of Use

The nanoparticle in the present composition can comprise any suitable inner core. For example, the inner core of the nanoparticle can comprise a polymeric particle core, a silica particle core, or a metal, e.g., gold, particle core. Any suitable polymeric particle core can be used. In some embodiments, the polymeric particle core can comprise an optical shift property. In other embodiments, the polymeric particle core can comprise a metal, e.g., gold, iron oxide or a quantum dot. In still other embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the nanoparticle supports the outer surface.

The nanoparticle can comprise a cellular membrane derived from any suitable cell The nanoparticle can comprise any suitable cellular membrane derived from an outer membrane vesicle. For example, the nanoparticle can comprise a secreted outer membrane vesicle (OMV) derived from a bacteria. In some embodiments, the outer membrane vesicle is combined with citrate-stabilized gold nanoparticles (AuNPs).

The nanoparticle in the present composition can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The nanoparticle in the present composition can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle in the present composition substantially lacks constituents of the cell, e.g., bacterial, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell, e.g., bacteria, from which the cellular membrane is derived.

In some embodiments, the nanoparticle in the present composition substantially maintains natural structural integrity or activity of the cellular membrane or the constituents of the cellular membrane. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity.

The nanoparticle in the present composition can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35 or 40 hours.

The outer surface of the nanoparticle in the present composition can comprise a synthetic membrane. In some embodiments, the nanoparticles in the present composition comprise a mixture of nanoparticles that comprise an outer surface comprising a cellular membrane, particularly bacterial outer membrane vesicles in certain embodiments, and nanoparticles that comprise an outer surface comprising a synthetic membrane.

The present composition can comprise the nanoparticles that comprise an outer surface comprising a cellular membrane, particularly outer membrane vesicles in certain embodiments, and nanoparticles that comprise an outer surface comprising a synthetic membrane in any suitable ratio. In some embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a cellular membrane. In other embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the present composition can comprise about 1-10% (w/w) of the nanoparticles that comprise an outer surface comprising a cellular membrane and about 90-99% (w/w) of the nanoparticles that comprise an outer surface comprising a synthetic membrane, about 11-25% (w/w) of the nanoparticles that comprise an outer surface comprising a cellular membrane and about 75-89% (w/w) of the nanoparticles that comprise an outer surface comprising a synthetic membrane, about 50% (w/w) of the nanoparticles that comprise an outer surface comprising a cellular membrane and about 50% (w/w) of the nanoparticles that comprise an outer surface comprising a synthetic membrane, about 51-75% (w/w) of the nanoparticles that comprise an outer surface comprising a cellular membrane and about 49-25% (w/w) of the nanoparticles that comprise an outer surface comprising a synthetic membrane, or about 90-100% (w/w) of the nanoparticles that comprise an outer surface comprising a cellular membrane and about 0-10% (w/w) of the nanoparticles that comprise an outer surface comprising a synthetic membrane.

The outer membrane vesicle coated on the outer surface of the nanoparticle in the present composition provides an improved anti-bacterial immune response over membrane vesicles alone.

The present composition can further comprise a suitable substance, e.g., a therapeutic agent, a prophylactic agent, a diagnostic or marker agent, a prognostic agent, an isolation agent, a monitoring agent, or a combination thereof. Exemplary therapeutic agent or prophylactic agent can be an anti-viral agent, an antibiotic, an anti-fungal agent, or an anti-protozoa agent. In some embodiments, the therapeutic agent or prophylactic agent is quinine. In other embodiments, the therapeutic agent or prophylactic agent is an antibiotic. Any suitable antibiotic can be used. For example, the antibiotic can be an inhibitor of cell wall synthesis, an inhibitor of protein synthesis, an inhibitor of membrane function, an inhibitor for folate pathway, or an inhibitor of nucleic acid synthesis function. Any suitable inhibitor of cell wall synthesis can be used. For example, the inhibitor of cell wall synthesis can be penicillin, cephalosporin, monobactam, penem, a glycopeptide, or a lipoglycopeptide.

In some embodiments, the present composition can further comprise exemplary antibiotic(s), or a combination thereof, listed in the above Table 1.

The therapeutic agent, the prophylactic agent, the vaccine agent, the diagnostic or marker agent, the prognostic agent, the isolation agent, the monitoring agent, or a combination thereof, can be comprised in any suitable location of the present composition. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle. In some embodiments, the therapeutic agent, the prophylactic agent, the diagnostic or marker agent, the prognostic agent, the isolation agent, the monitoring agent, or a combination thereof, can be comprised in the present composition but outside the nanoparticle.

The present composition can be made, stored, transported and/or used in any suitable formulation. In some embodiments, the present composition can further comprise a pharmaceutically acceptable carrier or excipient. In other embodiments, the present composition can be comprised in a medicament delivery system, a medical device or a consumer product. Any suitable medicament delivery system or medical device can be used. For example, the medicament delivery system or the medical device can be an implant, e.g., breast implant or an implant placed during or after bone surgery, a catheter, a sustained-release drug delivery system, or a dressing for healing of burn or other hard-to-heal wound. The present composition can be made, stored, transported and/or used in any suitable consumer product. For example, the consumer product can be a hygiene product, e.g., a disposable diaper. In still other embodiments, the present composition can be configured to be a part of scaffolds in tissue engineering.

In some embodiments, the methods can further comprise administering, to a subject, an exemplary antibiotic(s), or a combination thereof, as listed in the above Table 1.

The therapeutic agent, the prophylactic agent, the diagnostic or marker agent, the prognostic agent, the isolation agent, the monitoring agent, or a combination thereof, can be comprised in any suitable location in the composition used in the present methods. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle. In some embodiments, the therapeutic agent, the prophylactic agent, the diagnostic or marker agent, the prognostic agent, the isolation agent, the monitoring agent, or a combination thereof, can be comprised in the composition used in the present methods but outside the nanoparticle. In other embodiments, the therapeutic agent, the prophylactic agent, the diagnostic or marker agent, the prognostic agent, the isolation agent, the monitoring agent, or a combination thereof, can be administered to the subject separately from the composition used in the present methods. The composition used in the present methods and the additional substance can be administered to the subject simultaneously or sequentially.

In some embodiments, the present methods can further comprise administering a pharmaceutically acceptable carrier or excipient to the subject.

The composition used in the present methods can be administered using any suitable delivery mechanisms or techniques. In some embodiments, the composition can be administered alone. In other embodiments, the composition can be administered with a pharmaceutically acceptable carrier or excipient. In still other embodiments, the composition can be administered via a medicament delivery system, a medical device or a consumer product. Any suitable medicament delivery system or medical device can be used. The composition used in the present methods can be administered to the subject via any suitable route of administration.

In some embodiments, the composition can be administrated to the subject via rectal, nasal, topical, ocular, intramuscular, intraperitoneal, or subcutaneous route of administration.

Further exemplary embodiments of the invention are described as follows:
1. A nanoparticle comprising:
   a) an inner core comprising a non-cellular material; and
   b) an outer surface comprising a bacterial membrane.
2. The nanoparticle of embodiment 1, wherein the inner core non-cellular material comprises gold.
3. The nanoparticle of embodiment 1, wherein the cellular membrane is derived from a bacteria secreted outer membrane vesicle.
4. The nanoparticle of embodiment 1, wherein the bacteria is E. coli.
5. The nanoparticle of embodiment 1, wherein the cellular membrane comprises an immunogenic native antigen.
6. The nanoparticle of embodiment 1, wherein the nanoparticle further comprises a releasable cargo.
7. The nanoparticle of embodiment 6, wherein the releasable cargo is a therapeutic agent, a prophylactic agent, a diagnostic or marker agent, a prognostic agent, or a combination thereof.
8. A medicament delivery system, which comprises an effective amount of the nanoparticle of embodiment 1.
9. A pharmaceutical composition comprising an effective amount of the nanoparticle of embodiment 1 and a pharmaceutically acceptable carrier or excipient.
10. A method for treating or preventing a disease or condition in a subject in need comprising administering to said subject an effective amount of the nanoparticle of embodiment 1.
11. A process for making a nanoparticle comprising:
   a) combining an inner core comprising a non-cellular material, and an outer surface comprising a bacterial membrane; and
   b) exerting exogenous energy on the combination to form a nanoparticle comprising said inner core and said outer surface.
12. A bacteria specific immunogenic composition comprising an effective amount of a nanoparticle comprising an inner core comprising a non-cellular material, and an outer surface comprising an outer membrane vesicle derived from a bacteria.
13. A vaccine comprising the bacteria specific immunogenic composition of embodiment 12.
14. A method for treating or preventing a bacterial infection in a subject in need comprising administering to said subject an effective amount of the bacteria specific immunogenic composition of embodiment 12.
15. A pharmaceutical composition for treating or preventing a disease or condition associated with a bacteria, wherein said pharmaceutical composition comprises an effective amount of a nanoparticle comprising an inner core comprising a non-cellular material and an outer surface comprising an outer membrane vesicle derived from a bacteria.
16. A method for treating or preventing a disease or condition associated with a bacteria in a subject in need comprising administering to said subject an effective amount of the pharmaceutical composition of embodiment 15.
17. An immunogenic composition comprising an effective amount of a nanoparticle comprising an inner core comprising a non-cellular material, and an outer surface comprising a cellular membrane derived from an outer membrane vesicle derived from a bacteria.
18. A vaccine comprising the immunogenic composition of embodiment 17.
19. A method for eliciting an immune response to a cell membrane in a subject comprising administering to said subject an effective amount of the immunogenic composition of embodiment 17.
20. A method for protecting a subject against an infection comprising administering to said subject an effective amount of the vaccine of embodiment 18.

F. Example 1.

FIG. 1 is a schematic illustration of modulating antibacterial immunity via bacterial membrane-coated nanoparticles. Briefly, bacterial membrane was first collected from source bacteria in the form of secreted outer membrane vesicles (OMVs) and then mixed with citrate-stabilized gold nanoparticles (AuNPs) with a diameter of approximately 30 nm. Through an extrusion process, OMVs were fused with AuNPs, translocating the entire bacterial membrane onto gold surfaces to form bacterial membrane-coated AuNPs (BM-AuNPs). When injected subcutaneously into mice, BM-AuNPs elicited bacterium-specific immunity against the source bacteria.

Figure 2A:
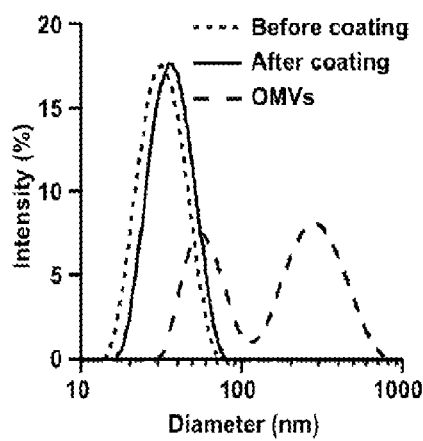
FIGS. 2A-2D illustrate the physicochemical characterization of BM-AuNPs.

The process of functionalizing AuNPs with bacterial membranes consists of two steps: collecting bacterial OMVs and fusing the OMVs onto the surfaces of AuNPs. In the study, E. coli OMVs were collected and purified by following established protocols.[19, 27] Dynamic light scattering (DLS) measurements showed that the collected vesicles had heterogeneous size distribution with diameters ranging from 30 to 300 nm (FIG. 2A). For membrane fusion, 30 nm citrate-stabilized AuNPs were mixed with OMVs and the mixture was extruded through a 50 nm porous polycarbonate membrane to generate BM-AuNPs. The mechanical force facilitated the fusion of OMVs with AuNPs. Owing to the high density of gold, following the extrusion, the excess OMVs and soluble compounds were removed by repeated low speed centrifugation.

Figure 2B:
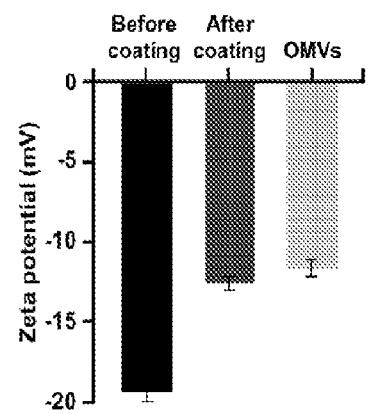
Figure 2C:
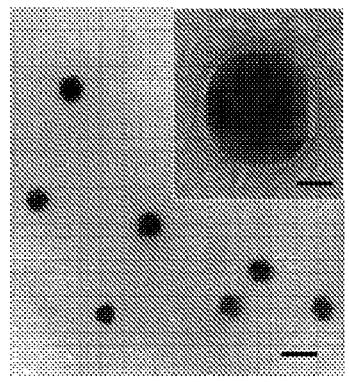
Figure 2D:
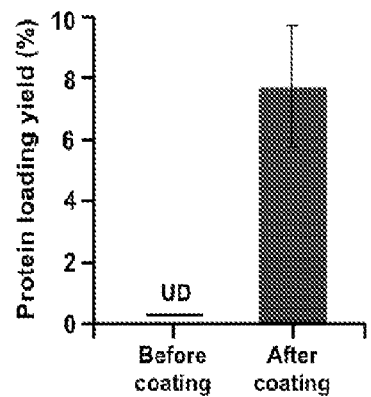

DLS measurements showed that the diameter of AuNPs increased from 30.3±0.2 nm to 41.9±0.5 nm upon bacterial membrane coating (FIG. 2A). This size increase is consistent with the addition of an approximately 6 nm thick lipid membrane, confirming the membrane coating onto the exterior surface of AuNPs.[28] Meanwhile, zeta potential measurements also indicated a successful membrane coating, as the value changed from −38.6±1.3 mV of bare AuNPs to −25.1±0.9 mV following the coating, comparable to the value measured from the OMVs (FIG. 2B). Next, the membrane coating was confirmed by examining the morphology of BM-AuNPs with transmission electron microscopy (TEM). Under the microscope, all nanoparticles showed a clear spherical core-shell structure, reflecting the enclosure of gold cores in a thin shell with a thickness of approximately 6 nm (FIG. 2C). The membrane coating was further verified with a protein bicinchoninic acid (BCA) assay. While the bare AuNPs showed the absence of detectable protein content, tests on BM-AuNPs showed a significant increase in absorbance at 562 nm, implying the presence of protein content on the nanoparticles. Further quantification indicated a protein loading yield, defined as the weight ratio of immobilized proteins to the gold nanoparticles, of approximately 7.9±2.0 wt % (FIG. 2d).

FIG. 2 represents the physicochemical characterization of BM-AuNPs. FIG. 2A is the Hydrodynamic sizes (diameter, nm) and FIG. 2B is the surface zeta potentials (mV) of AuNPs before coating and after coating, in comparison with those of OMVs. FIG. 2C is a representative TEM image showing the spherical core-shell structure of the BM-AuNPs negatively stained with uranyl acetate (scale bar, 50 nm). Inset: a zoomed-in view of a single BM-AuNP (scale bar, 10 nm). FIG. 2D is the quantification of protein concentration of AuNPs before and after the membrane coating by using a BCA assay. Protein loading yield is defined as the weight ratio of immobilized proteins to the gold nanoparticles.

Membrane coating drastically improved the nanoparticle buffer stability. When bare AuNPs were transferred from 2 mM citrate storage buffer into 1×PBS, the characteristic cherry red color of the AuNPs faded immediately, suggesting a rapid destabilization and aggregation of AuNPs, likely due to the increase of buffer ionic strength (FIG. 3A). On the contrary, when BM-AuNPs were transferred from 2 mM citrate into 1×PBS, the cherry red color remained unchanged, indicating the preservation of particle stability due to the membrane coating. Similar phenomena were also observed by using 100% fetal bovine serum instead of 1×PBS. Notably, vesicles generated from extruding OMVs without using AuNP cores was highly unstable, as their size increased rapidly from 50 nm to above 100 nm within 4 h. In contrast, size variation of BM-AuNPs was negligible, further confirming a higher stability conferred by membrane coating (FIG. S1). Collectively, these results demonstrated the mutual benefits between the OMVs and the AuNPs. That is, the membrane coating effectively enhanced AuNP stability in biological buffers, while the AuNP cores template the OMVs into uniformly sized nanoparticles and also ensure adequate nanoparticle stability for downstream in vivo applications.

In addition to buffer stability, we also examined the affinity of the coated membrane to the gold cores by using a fluorescein isothiocyanate (FITC)-thiol conjugate, which is a fluorescent probe that can be quenched when bound to the exposed surface of bare AuNPs.[28] The fluorescence spectrum of the FITC-thiol conjugate in solution showed a peak at 520 nm, characteristic of FITC's emission (FIG. 3B). Upon mixing with bare AuNPs, the fluorescence was significantly quenched, indicating the probe's close association with surfaces of the nanoparticles. In contrast, when BM-AuNPs were mixed with the conjugates under the same conditions, the quenching of FITC emission was largely absent, indicating that the highly reactive thiol groups were unable to replace the membrane coating. A slight decrease in fluorescence intensity observed upon the mixing of FITC-thiol and BM-AuNPs was attributable to the long-range fluorescence quenching effect of AuNPs. In addition, the sample showed no further decrease in fluorescence over a span of 72 h. Together, these results demonstrated a strong association of the membrane to the AuNPs, which effectively shielded the gold surfaces.

FIGS. 3A-3B represent the stability and membrane-core affinity of BM-AuNP. FIG. 3A is Both bare AuNPs and BM-AuNPs are stable in 2 mM citrate storage buffer. However, in 1×PBS, bare AuNPs rapidly aggregate while BM-AuNPs remain stable. FIG. 3B is a fluorescence quenching assay shows the strong affinity between the coated bacterial membrane and the gold cores. Fluorescence spectra were taken from i) FITC-thiol alone, ii) FITC-thiol mixed with BM-AuNPs, and iii) FITC-thiol mixed with bare AuNPs. The concentrations of FITC-thiol and AuNP are 1 nM and 0.025 nM (equivalent to 50 μg mL$^{-1}$), respectively.

Figure 9A:
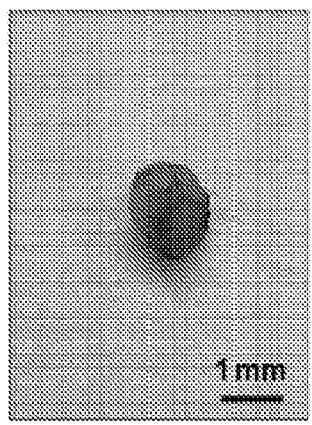
FIGS. 9A-9C illustrate an effect of BM-AuNP size on its lymph node transport. Mice were injected with 2.5 µg (50 µg/mL) BM-AuNPs of 30 nm and 90 nm, respectively, via the tail base. After 24 h, the lumbar and sacral lymph nodes were collected.
Figure 9B:
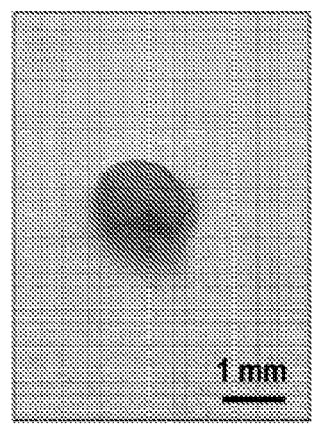
Figure 9C:
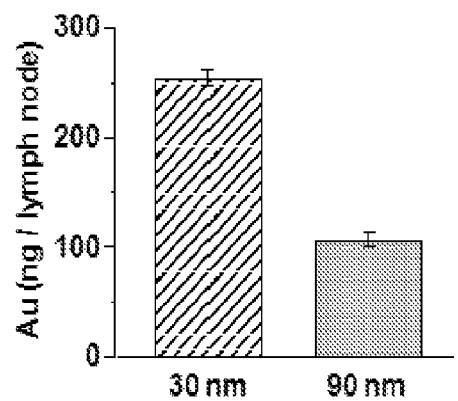

After having confirmed the coating of bacterial membranes onto AuNPs, we proceeded to evaluate the vaccine potential of BM-AuNPs. To this end, we first examined their efficiency in activating DCs in vivo. Nanoparticles were subcutaneously injected at the tail base of each mouse and then the upregulation of activation markers by DCs in the draining lymph nodes was examined.[29] In the study, we divided the mice into three groups and injected them with BM-AuNPs, OMVs, and PBS, respectively. Herein, natural OMVs were chosen as a control group as opposed to vesicles made by extruding OMVs because the latter had poor stability in PBS. Twelve hours after the injection, cells in the lumbar and sacral lymph nodes were collected and CD11c+ DC frequencies were counted. In the mice injected with BM-AuNPs and OMVs, DCs isolated from the lymph nodes displayed considerably higher frequencies of CD11c+ DCs than the mice injected with PBS, suggesting the elevated recruitment of DCs into these lymph nodes (FIG. 4A). Between these two groups, a higher frequency was observed in the group injected with BM-AuNPs than the OMV-injected group (p=0.0096), suggesting a higher efficacy of BM-AuNPs in boosting CD recruitment. The efficacy of BM-AuNPs and OMVs in eliciting DC maturation was compared. In both groups, CD11c+ DCs isolated from lumbar and sacral lymph nodes displayed a shift from the immature to the mature phenotype through upregulation of the co-stimulatory molecules CD40, CD80, and CD86 (FIG. 4B). Further quantification of the pencentage of CD11c+ DCs based on the histograms showed that the DC maturation level induced by BM-AuNPs was significantly higher than that induced by the OMVs alone (FIG. 4C). It has been reported that the transport rate of macromolecules and nanoparticles injected through the mouse tail base to the lumbar and sacral lymph nodes as well as subsequent DC activation efficacy are inversely correlated to size.[29, 30] Indeed, BM-AuNPs made with larger AuNPs (90 nm in diameter) showed a significantly reduced accumulation in the lymph nodes of mice as compared to smaller BM-AuNPs made with 30 nm AuNPs (FIG. 9C). Hence, the potent activation of DCs by BM-AuNPs indicates not only proper bacterial membrane coating on the particles but also highlights the advantage of using small sized nanoparticles for immune activation.

FIGS. 4A-4C represent BM-AuNPs activating DCs in the draining lymph nodes in vivo. FIG. 4A is the percentage CD11c+ cells in a total of 20,000 lymphocytes from naive mice or mice vaccinated with either OMVs or BM-AuNPs (2.5 μg gold) 12 h after the subcutaneous injection. Data are shown with mean frequencies±SEM (standard error of the mean) measured per lymph node (*p<0.05). FIG. 4B is a representative flow cytometry analysis of surface maturation markers (CD40, CD80, and CD86) on CD11c+ DCs from lumbar and sacral lymph nodes of the mice (n=5). FIG. 4C is the quantification of the pencentage of CD11c+ DCs based on the histograms in (b). Data are shown with mean percentage±SEM (*p<0.05, **p<0.01). Three independent experiments were carried out.

Bacterium-specific B cell responses were assessed by examining the elicitation of E. coli-specific antibodies. In the study, a vaccination schedule was adopted that included a prime on day 0 and two booster vaccinations on day 7 and day 14, respectively.[17] Naive mice and mice vaccinated with OMVs served as two control groups. To examine whether the response was dose-dependent, we administered the mice with either 0.2 or 0.02 μg antigen per injection. During the immunization process, sera were obtained from mice of all groups and E. coli-binding IgG titers were measured. Determination of antibody responses on day 21 showed that BM-AuNPs induced significantly higher E. coli-specific antibody titers in comparison to the OMVs (p=0.0016 at 0.2 μg antigen/dose, p=0.0148 at 0.02 μg antigen/dose, FIG. 5A). Such enhancement in antibody response by BM-AuNPs was also observed in a time-course study. In the first 21 days of the immunization, a continuous rise in *E. coli*-binding IgG was detected in both BM-AuNP- and OMV-immunized mice, but not in naïve mice (FIG. 5B). Afterward, the IgG titer levels remained stable in all groups throughout the study, where enhancements by approximately 3- and 5-fold (geometric means) were measured for the BM-AuNP groups as compared to the OMV groups at dosages of 0.2 and 0.02 µg antigen (n=7), respectively. In addition to the titer levels, we also examined the quality of the antibody response raised against the source bacteria by assessing the avidity of sera from the mice. Compared to OMV vaccinated mice, antibody from BM-AuNP vaccinated mice showed a significantly higher avidity index to the *E. coli* bacteria (p=0.027, n=7, FIG. 5C). Overall, vaccination with BM-AuNPs generates antibody responses that are durable and of higher avidity than those elicited by OMVs only, indicating the potential of BM-AuNPs for enhancing antibacterial immunity.

Figure 5A:
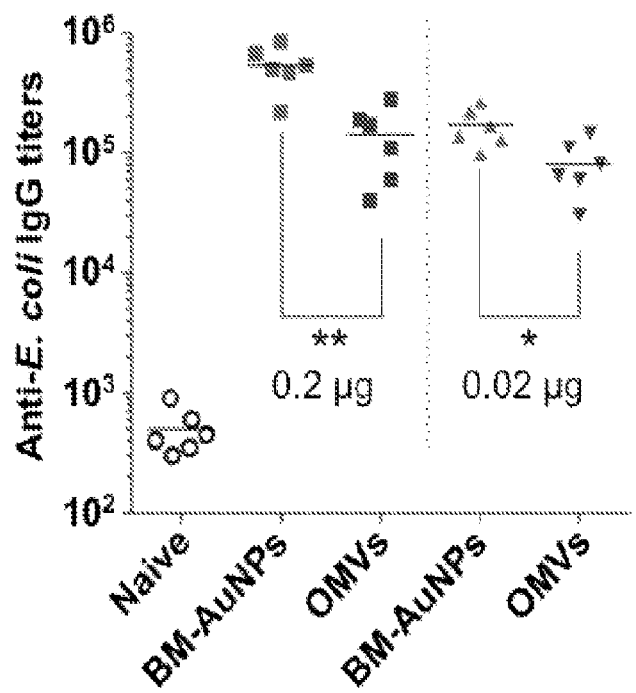
FIGS. 5A-5C illustrate the BM-AuNPs eliciting strong bacterium-specific antibody responses in vivo.
Figure 5B:
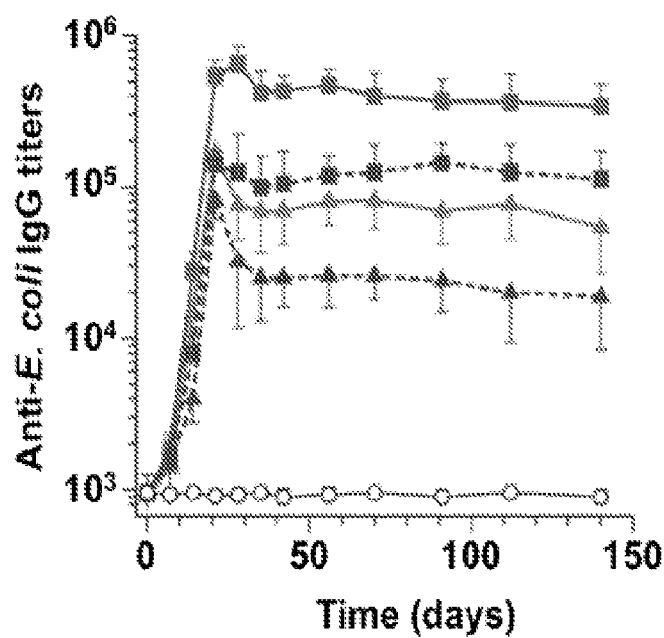
Figure 5C:
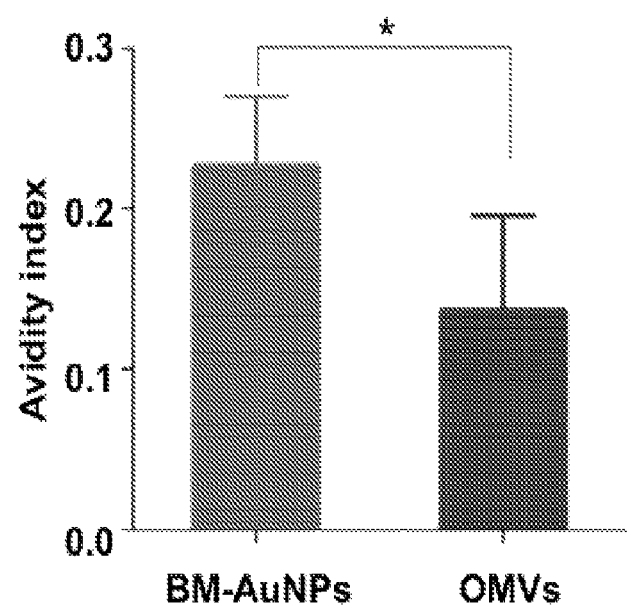

FIGS. 5A-5C represent the BM-AuNPs eliciting strong bacterium-specific antibody responses in vivo. FIG. 5A is the Anti-*E. coli* IgG titres at day 21 (n=6). Black lines indicate geometric means. Naive mice were monitored as a negative control (open circles). FIG. 5B is the time course of anti-*E. coli* IgG titres in naive mice (open circles) and mice immunized with 0.2 µg antigen/dose BM-AuNPs (red squares), 0.2 µg antigen/dose OMVs (blue squares), 0.02 µg antigen/dose BM-AuNPs (red triangles), and 0.02 µg antigen/dose OMVs (blue triangles), respectively (n=6). FIG. 5C is the quantified avidity index of the anti-sera from immunized mice (0.2 µg antigen/dose) binding to *E. coli* bacteria (n=6). *p<0.05, **p<0.01.

Figure 6A:
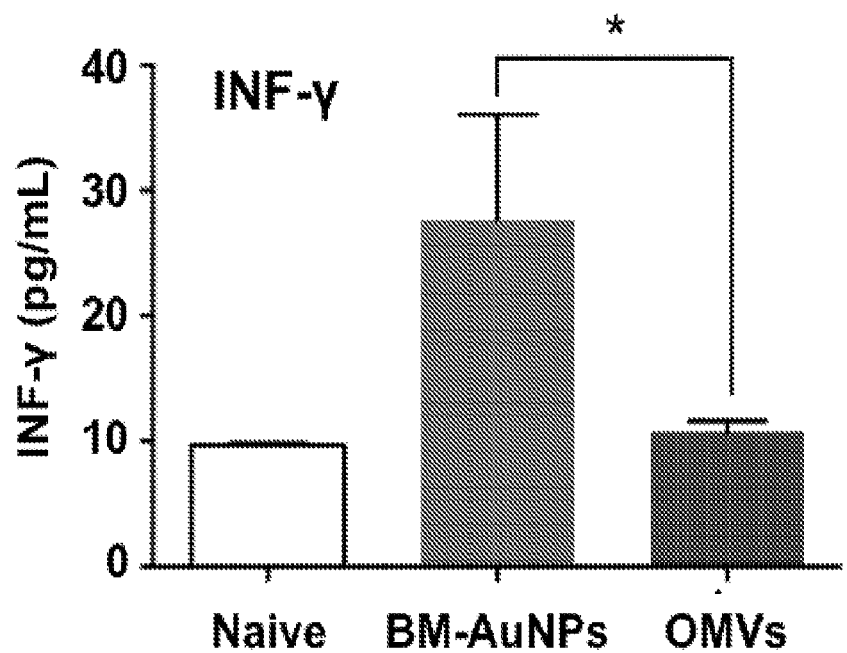
FIGS. 6A-6C illustrate the BM-AuNPs inducing pronounced bacterium-specific T cell activation in vivo. The mice (n=10) were immunized with 0.2 µg antigen/dose BM-AuNPs or OMVs. Naive mice were tested in parallel as a negative control. On day 21, splenic cells were collected and stimulated with *E. coli* bacteria. After 72 h of co-culturing with the bacteria, the levels of FIG. 6A IFN-γ, FIG. 6B IL-17, and FIG. 6C IL-4 in the medium were quantified using an ELISA. *p<0.05. Bars represent means±SD (n=10). UD=undetectable by ELISA.

Finally, the effects of BM-AuNP immunization on activating bacterium-specific T cell responses was examined. The role of T cell-mediated immunity has become increasingly recognized in generating effective protection against a variety of infections. In the study, mice were immunized with 0.2 µg antigen/dose of BM-AuNPs or OMVs, following the aforementioned schedules. We collected the splenic cells on day 21 and stimulated them with inactivated *E. coli* bacteria for 72 h. T cell activation was quantified by measuring levels of three cytokines in the cell culture: interferon gamma (IFNγ), interleukin 17 (IL-17), and interleukin 4 (IL-4). The results showed that the levels of IFN-γ and IL-17 production were higher in mice immunized with either BM-AuNPs or OMVs compared to the naïve mice, indicating successful *E. coli*-specific T cell activation (FIG. 6A,B). The comparison also showed that mice immunized with BM-AuNPs produced significantly higher levels of IFN-γ (p=0.0468, n=10) and IL-17 (p=0.0397, n=10) than OMV-immunized mice, implying a higher efficacy of BM-AuNPs in activating T cells. Meanwhile, production of IL-4, the key cytokine of Th2 cells, was undetectable in all groups (FIG. 6C). The elevated production of IFN-γ and IL-17 but not IL-4 demonstrated strong Th1 and Th17 biased cell responses against the bacterial infection.

Figure 6B:
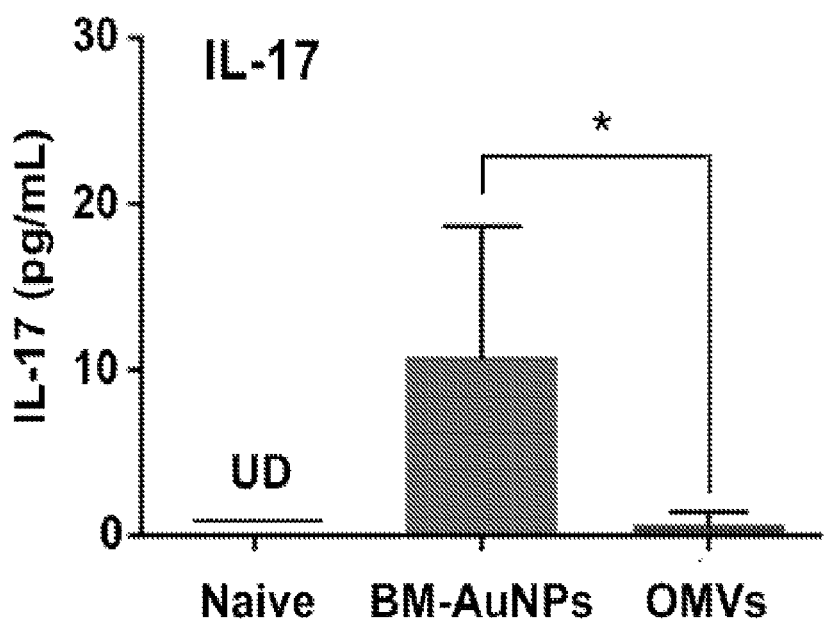
Figure 6C:
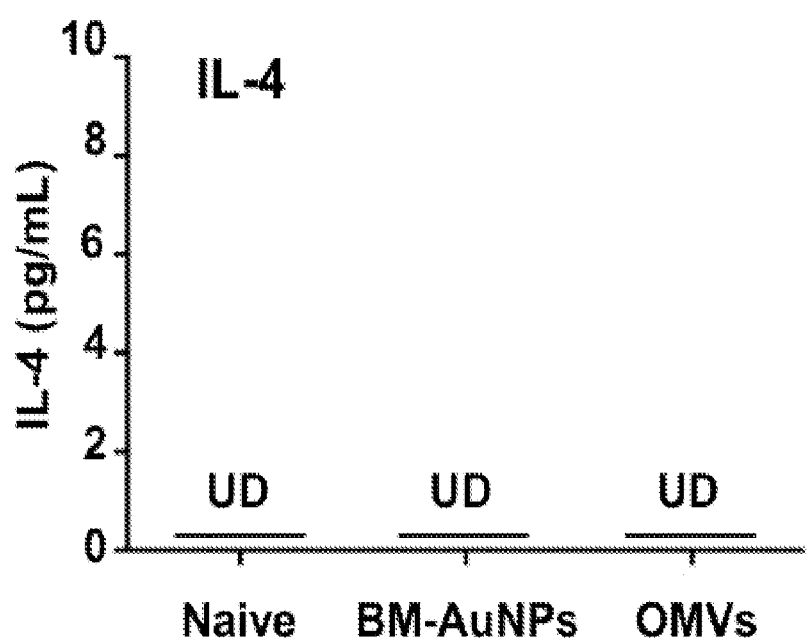

FIGS. 6A-6C represent the BM-AuNPs inducing pronounced bacterium-specific T cell activation in vivo. The mice (n=10) were immunized with 0.2 µg antigen/dose BM-AuNPs or OMVs. Naive mice were tested in parallel as a negative control. On day 21, splenic cells were collected and stimulated with *E. coli* bacteria. After 72 h of co-culturing with the bacteria, the levels of FIG. 6A IFN-γ, FIG. 6B IL-17, and FIG. 6C IL-4 in the medium were quantified using an ELISA. *p<0.05. Bars represent means±SD (n=10). UD=undetectable by ELISA.

The design of BM-AuNPs reported in this study seeks synergy between bacterial membranes and synthetic nanoparticles to generate a unique and robust antibacterial vaccine. Using bacterial OMVs as membrane materials, BM-AuNPs contain a large number of immunogenic antigens with intrinsic adjuvant properties. In addition, the faithful translocation of the entire bacterial membranes via a top-down approach onto the nanoparticle surfaces preserves critical immune determinants such as the pathogen associated-molecular patterns. As a result, the BM-AuNPs closely mimic antigen presentation by bacteria to the immune cells. On the other hand, using AuNPs as coating template allows a range of nanoparticle physicochemical properties to be precisely tailored for desired immune responses. In this study, the AuNP-templated membrane coating transformed OMVs from widely polydispersed vesicles into uniformly distributed ultra-small nanoparticles and subsequently resulted in rapid DC activation in vivo. Moreover, the AuNP-templated coating also led to strong association between the membrane and the core, which likely reinforced the multivalent display of epitopes on the bacterial membranes. Such strengthened interactions between the antigens and the nanoparticle architecture have been attributed to the enhanced antibody and endogenous T cell responses in other nanoparticle-based vaccine platforms.[17, 31, 32] Taken together, the bacterial membranes and the AuNP cores mutually benefit each other, synergistically generating enhanced antibacterial immune responses.

Using bacterial membranes to coat synthetic nanoparticles opens many opportunities for designing effective antibacterial vaccines. For example, secretion of OMVs seems like a conserved process not only found on Gram-negative but also an increasing number of Gram-positive bacteria; therefore, the use of OMVs as membrane materials for nanoparticle coating is potentially applicable to a wide range of bacteria.[33, 34] In addition, genetic engineering has been successful in developing OMVs that express multiple mutants or exogenous antigens.[35, 36] These engineered OMVs can be also exploited as membrane materials for broadening immune protection. Meanwhile, the cellular membrane-coated nanoparticle, since its first development, has made significant progress. Particularly, a wide range of synthetic cores have been successfully coated, including those made of polymers,[12, 16, 17, 37] silica,[14] and gold.[28, 38] These synthetic nanoparticles, already with intensive applications in drug delivery, offer exciting opportunities to manipulate nanoparticle characteristics for even broader biomedical applications. Together, these technological advances will benefit the development of bacterial membrane-coated nanoparticles with numerous implications toward effective and safe antibacterial vaccines.

Example 2

Figure 7:
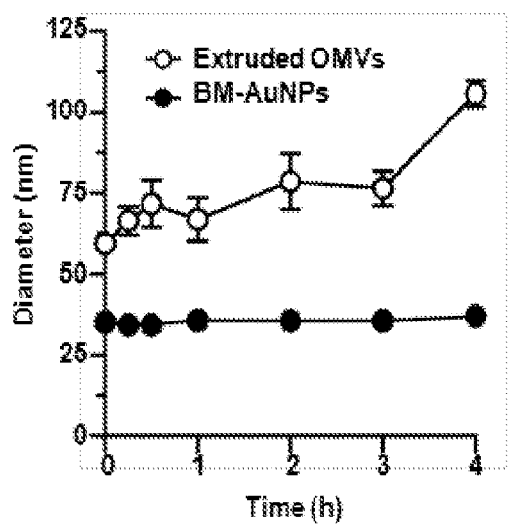
FIG. 7 illustrates the hydrodynamic sizes of BM-AuNPs (solid circles) and vesicles formed by extruding OMVs through a polycarbonate membrane with 50 nm pores (open circles). The sizes were measured by dynamic light scattering (DLS) in PBS buffer.

FIG. 7 represents the hydrodynamic sizes of BM-AuNPs (solid circles) and vesicles formed by extruding OMVs through a polycarbonate membrane with 50 nm pores (open circles). The sizes were measured by dynamic light scattering (DLS) in PBS buffer.

The collected OMVs were first extruded through a 50 nm polycarbonate porous membrane to generate small vesicles. The resulting vesicles and the corresponding BM-AuNPs were then suspended in 1×PBS. Their hydrodynamic sizes were monitored with dynamic light scattering (DLS). It was found that the size of extruded OMVs quickly increased from 50±3.1 nm immediately after extrusion to 102±8.9 nm at 4 h post extrusion. In contrast, the corresponding BM-AuNPs showed negligible size change during this time period. The observed size increase of the extruded OMVs is likely due to fusion among these small vesicles, as the extrusion process may disrupt membrane rigidity of the OMVs. This finding also highlights the critical role played by AuNP cores to template membrane coating, which not only template the OMVs into uniformly sized nanoparticles but also ensure adequate nanoparticle stability for further in vivo studies.

To study how BM-AuNP size affects its transport to lymph nodes, bacterial OMVs were coated onto AuNPs with two different sizes, 30 nm and 90 nm (diameter), respectively. The preparation and characterization of BM-AuNPs made with 30 nm AuNPs were reported in the main manuscript and FIG. 2. To prepare BM-AuNPs made with 90 nm AuNPs, we purchased citrate-stabilized AuNPs with a diameter of approximately 90 nm and a concentration of 50 μg mL$^{-1}$ (nanoComposix, Inc). The AuNPs were then mixed with OMVs and then extruded 7 times through a 100 nm polycarbonate porous membrane with an Avanti mini extruder. Following the extrusion, we removed the excess OMVs and soluble compounds by repeated low speed centrifugation (approximately 9000×g). Transmission electron microscopy (TEM) image revealed a similar core-shell structure as that of the 30 nm BM-AuNPs (FIG. 8).

Figure 8:
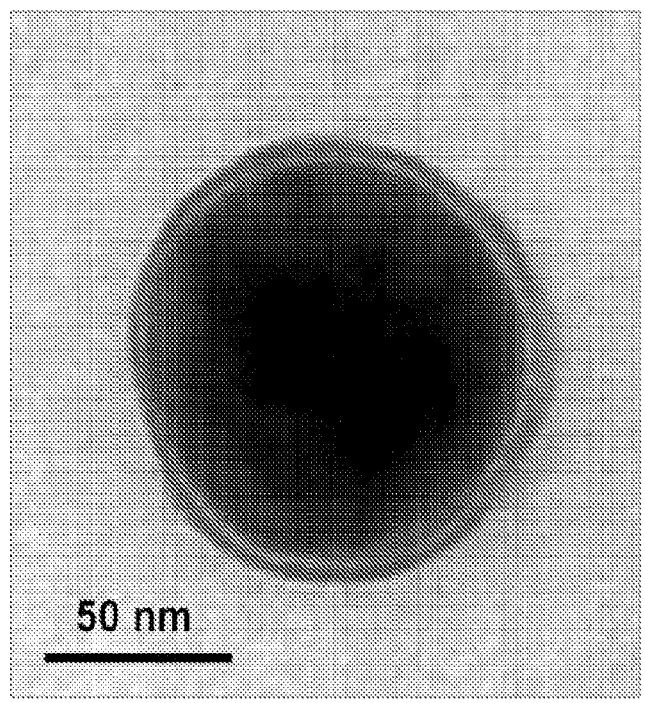
FIG. 8 is a representative TEM image showing the spherical core-shell structure of the BM-AuNP made with AuNP of 90 nm diameter. The sample was negatively stained with uranyl acetate before TEM imaging.

FIG. 8 is a representative TEM image showing the spherical core-shell structure of the BM-AuNP made with AuNP of 90 nm diameter. The sample was negatively stained with uranyl acetate before TEM imaging.

To study the lymph node transport of BM-AuNPs, mice were injected with 2.5 μg (50 μg/mL) BM-AuNPs of 30 nm and 90 nm, respectively, through their tail base. After 24 h, the lumbar and sacral lymph nodes were collected. The lymph nodes from the mice showed obvious color difference between the 30 nm BM-AuNPs and the 90 nm BM-AuNPs (FIGS. 9A,9B). Specifically, lymph nodes from mice injected with 30 nm BM-AuNPs showed dark grey (FIG. 9A), whereas those from mice injected with 90 nm BM-AuNPs showed an opulent color of natural tissue (FIG. 9B).

Gold concentration in the collected lymph nodes was quantified by using inductively coupled plasma mass spectrometry (ICP-MS). The ICP-MS measurements found that approximately 0.25 μg 30 nm BM-AuNPs or 0.1 μg 90 nm BM-AuNPs accumulated in each lymph node (FIG. 9C). When converted to nanoparticle numbers, 30 nm BM-AuNPs accumulated 67 times higher than 90 nm ones. When converted to nanoparticle surface area, which directly correlates to the amount of bacterial membrane materials, the surface area of 30 nm BM-Au NPs in the lymph node is about 7.5 times higher than 90 nm ones.

The invention provides a new and robust antibacterial vaccine strategy by coating natural bacterial membranes collected from bacterium-secreted OMVs onto small AuNPs. The resulting BM-AuNPs showed significantly enhanced stability in biological buffer solutions, with the coated membrane strongly associated with the AuNP cores. When injected subcutaneously, BM-AuNPs induced rapid activation and maturation of DCs in lymph nodes. Furthermore, vaccination with BM-AuNPs generated strong and durable antibody responses with higher avidity than those elicited by OMVs only. Compared to OMVs, BM-AuNPs also induced an elevated production of IFN-γ and IL-17 but not IL-4, indicating their ability to generate Th1 and Th17 biased cell responses against the source bacteria. Taken together, the bacterial membranes and the AuNP cores mutually benefit each other, generating a synergy for enhanced immune responses. Overall, using bacterial membranes to coat synthetic nanoparticles holds a significant potential for designing effective antibacterial vaccines.

Materials and Methods

Bacterial culture and collection of bacterial outer membrane vesicles (OMVs). *Escherichia coli* (*E. coli*) bacteria (strain DH5α) were cultured on Luria broth (LB) agar overnight at 37° C. Then a single colony was inoculated into LB medium. Following the inoculation, the medium was cultured in a rotary shaker at 37° C. for 10 h and then refreshed with LB medium at a 1:100 dilution. The culture continued for another 3 h until the OD$_{600}$ value of the medium reached approximately 1.0, indicating the logarithmic growth phase. *E. coli* OMVs were collected by following published protocols[19, 27]. Briefly, 250 mL bacterial culture was centrifuged at 4000×g for 10 min to remove the bacteria, followed by filtering through a 0.45-μm vacuum filter. The filtrate was then concentrated by using Amicon centrifugal filters with a molecular weight cutoff of 100 kDa (Millipore). The concentrated medium was then centrifuged with an SW 41 Ti rotor (Beckman Instruments) at 150,000×g for 2 h at 4° C. The OMV pellet was resuspended in water and stored at −80° C. for further experiments.

BM-AuNP Preparation and Characterization. Citrate-stabilized gold nanoparticles (bare AuNPs) with a diameter of approximately 30 nm and a concentration of 50 μg mL$^{-1}$ (nanoComposix, Inc) were used for all studies. To fuse with the OMVs, AuNPs were mixed with OMVs and then extruded 7 times through a 50-nm polycarbonate porous membrane with an Avanti mini extruder. Given the high density of gold, following the extrusion, we removed the excess OMVs and soluble compounds via repeated low speed centrifugation (approximately 9000×g). Particle size (diameter, nm), polydispersity, and surface charge (zeta potential, mV) of the resulting BM-AuNPs were measured by dynamic light scattering (DLS) on a Zetasizer Nano ZS (model ZEN3600 from Malvern Instruments). A FITC-thiol conjugate was synthesized and used to test the stability and the shielding effect of the bacterial membrane coating as previously described.[28] In the study, the FITC-thiol was added into BM-AuNPs and bare AuNPs (without bacterial membrane coating), separately, and then the fluorescence intensity at 520 nm was measured by using a Tecan Infinite M200 microplate reader. Bacterial membrane coating was further examined by using transmission electron microscopy (TEM). Briefly, 1 mL of BM-AuNPs (50 μg mL$^{-1}$) was carefully centrifuged to concentrate into a final volume of about 10 μL. Then 3 μL of concentrated particle suspension was deposited onto a glow-discharged carbon-coated copper grid. Five minutes after the sample was deposited, the grid was rinsed with 10 drops of distilled water, followed by staining with a drop of 1% uranyl acetate. The grid was subsequently dried and visualized using an FEI 200 kV Sphera microscope. Total protein content on the nanoparticles was determined by using a BCA kit (Thermo Scientific Pierce) to measure the absorbance at 562 nm in comparison with bovine serum albumin protein standard.

Animal care and injections. 6-week-old male CD-1 mice (Charles River Laboratories) were housed in the Animal Facility at the University of California San Diego under federal, state, local, and National Institutes of Health guidelines for animal care. In the study, BM-AuNPs, OMVs, and PBS were injected as a bolus of 50 μL into the base of the mouse tail through a 30-gauge needle[29]. No inflammation was observed at the sites of injection.

Flow cytometry analysis of dendritic cell (DC) activation. DC activation was tested by removing lumbar and sacral lymph nodes 24 h after injection of BM-AuNPs, OMVs, or PBS. Single cell suspensions were prepared by teasing the lymph nodes with 26-gauge needles and digesting in Collagenase D (Roche Applied Science) for 20 min at 37° C. The tissue suspension was passed through a 40-μm membrane (BD Biosciences) to produce a single cell suspension.

Cells were then washed, blocked, and stained with antibodies against CD11c, CD40, CD80, and CD86. Flow cytometry analysis was performed on a BD Biosciences FACS Calibur HTS. To analyze frequency, a total of 20,000 cells were counted.

Immunization studies. Groups of mice (n=6) were immunized subcutaneously at the tail base with the indicated doses of BM-AuNPs, OMVs, or PBS on day 0, 7 and 14, respectively. At pre-determined time points, sera were collected and quantified for anti-E. coli IgG antibodies by ELISA on E. coli bacterium-coated plates prepared by following a published protocol.[17] Titers were defined as the lowest serum dilution at which the ELISA OD reading was ≥0.5. Avidity measurements were performed by incubating plates with 6 M urea for 15 min at 20° C. to remove weakly bound IgG prior to addition of detection antibodies.[17] The avidity index was defined as the ratio of IgG titer with 6 M urea to IgG titer without urea. Statistical analysis was performed with GraphPad Prism using an unpaired two-tailed t-test.

T cell response studies. Groups of mice (n=10) were immunized subcutaneously at the tail base with the indicated dosages of BM-AuNPs, OMVs, or PBS on day 0, 7 and 14, respectively. On day 21, the mice were sacrificed and their spleens were collected. To prepare single cell splenocyte suspensions, the collected spleens were minced and digested by Collagenase D. Then the tissue suspension was passed through a 40-μm cell strainer and red blood cells were removed by selected lysis. The collected cells were washed and resuspended with PBS. The cells in each suspension were then counted and seeded onto 12-well plates with a density of $2 \times 10^5$ cells/well. To each well, $1 \times 10^7$ CFU of E. coli bacteria, killed by formalin fixation and thoroughly washed with PBS, were added. The cells were incubated for 72 h at 37° C. and 5% $CO_2$. Following the incubation, supernatants from each well were collected and the concentrations of cytokines including IFNγ, IL-4, and IL-17 were quantified using ELISA Ready-SET-Go assays (eBiosciences). Statistical analysis was performed with GraphPad Prism using an unpaired two-tailed t-test.

REFERENCES

1. Mendoza, N.; Ravanfar, P.; Satyaprakah, A.; Pillai, S.; Creed, R. *Dermatol. Ther.* 2009, 22, 129-142.
2. Germain, R. N. *Immunity* 2010, 33, 441-450.
3. Spellberg, B.; Bartlett, J. G.; Gilbert, D. N. *New Engl. J. Med.* 2013, 368, 299-302.
4. Kaufmann, S. H. E. *Nat. Rev. Microbiol.* 2007, 5, 491-504.
5. Rappuoli, R.; Aderem, A. *Nature* 2011, 473, 463-469.
6. Koff, W. C.; Burton, D. R.; Johnson, P. R.; Walker, B. D.; King, C. R.; Nabel, G. J.; Ahmed, R.; Bhan, M. K.; Plotkin, S. A. *Science* 2013, 340, article 1232910.
7. Swartz, M. A.; Hirosue, S.; Hubbell, J. A. *Sci. Transl. Med.* 2012, 4, article 148rv9.
8. Irvine, D. J.; Swartz, M. A.; Szeto, G. L. *Nat. Mater.* 2013, 12, 978-990.
9. Leleux, J.; Roy, K. *Adv. Healthcare Mater.* 2013, 2, 72-94.
10. Balmert, S. C.; Little, S. R. *Adv. Mater.* 2012, 24, 3757-3778.
11. Gong, Y.-k.; Winnik, F. M. *Nanoscale* 2012, 4, 360-368.
12. Hu, C.-M. J.; Fang, R. H.; Zhang, L. *Adv. Healthcare Mater.* 2012, 1, 537-547.
13. Hu, C.-M. J.; Zhang, L.; Aryal, S.; Cheung, C.; Fang, R. H.; Zhang, L. *Proc. Natl. Acad. Sci. U.S.A.* 2011, 108, 10980-10985.
14. Parodi, A., et al. *Nat. Nanotechnol.* 2013, 8, 61-68.
15. Fang, R. H.; Hu, C.-M. J.; Luk, B. T.; Gao, W.; Copp, J. A.; Tai, Y.; O'Connor, D. E.; Zhang, L. *Nano Lett.* 2014, 14, 2181-2188.
16. Hu, C.-M. J.; Fang, R. H.; Copp, J.; Luk, B. T.; Zhang, L. *Nat. Nanotechnol.* 2013, 8, 336-340.
17. Hu, C.-M. J.; Fang, R. H.; Luk, B. T.; Zhang, L. *Nat. Nanotechnol.* 2013, 8, 933-938.
18. Poetsch, A.; Wdlters, D. *Proteomics* 2008, 8, 4100-4122.
19. Lee, E.-Y., et al. *Proteomics* 2007, 7, 3143-3153.
20. Kuehn, M. J.; Kesty, N. C. *Genes Dev.* 2005, 19, 2645-2655.
21. Hu, C.-M. J.; Fang, R. H.; Luk, B. T.; Chen, K. N. H.; Carpenter, C.; Gao, W.; Zhang, K.; Zhang, L. *Nanoscale* 2013, 5, 2664-2668.
22. Luk, B. T.; Hu, C.-M. J.; Fang, R. H.; Dehaini, D.; Carpenter, C.; Gao, W.; Zhang, L. *Nanoscale* 2014, 6, 2730-2737.
23. Unal, C. M.; Schaar, V.; Riesbeck, K. *Semin. Immunopathol.* 2011, 33, 395-408.
24. Acevedo, R., et al. *Front. Immunol.* 2014, 5, 121-121.
25. Hurst, S. J.; Lytton-Jean, A. K. R.; Mirkin, C. A. *Anal. Chem.* 2006, 78, 8313-8318.
26. Chithrani, B. D.; Ghazani, A. A.; Chan, W. C. W. *Nano Lett.* 2006, 6, 662-668.
27. Kim, O. Y., et al. *J. Immunol.* 2013, 190, 4092-4102.
28. Gao, W.; Hu, C.-M. J.; Fang, R. H.; Luk, B. T.; Su, J.; Zhang, L. *Adv. Mater.* 2013, 25, 3549-3553.
29. Reddy, S. T.; van der Vlies, A. J.; Simeoni, E.; Angeli, V.; Randolph, G. J.; O'Neill, C. P.; Lee, L. K.; Swartz, M. A.; Hubbell, J. A. *Nat. Biotechnol.* 2007, 25, 1159-1164.
30. Jewell, C. M.; Lopez, S. C. B.; Irvine, D. J. *Proc. Natl. Acad. Sci. U.S.A.* 2011, 108, 15745-15750.
31. Moon, J. J., et al. *Nat. Mater.* 2011, 10, 243-251.
32. Moon, J. J.; Suh, H.; Li, A. V.; Ockenhouse, C. F.; Yadava, A.; Irvine, D. J. *Proc. Natl. Acad. Sci. U.S.A.* 2012, 109, 1080-1085.
33. Gurung, M., et al. *PLoS One* 2011, 6, article e27958.
34. Thay, B.; Wai, S. N.; Oscarsson, *J. PLoS One* 2013, 8, article e54661.
35. Chen, D. J.; Osterrieder, N.; Metzger, S. M.; Buckles, E.; Doody, A. M.; DeLisa, M. P.; Putnam, D. *Proc. Natl. Acad. Sci. U.S.A.* 2010, 107, 3099-3104.
36. Gujrati, V.; Kim, S.; Kim, S.-H.; Min, J. J.; Choy, H. E.; Kim, S C.; Jon, S. *ACS Nano* 2014, 8, 1525-1537.
37. Li, L.-L.; Xu, J.-H.; Qi, G.-B.; Zhao, X.; Yu, F.; Wang, H. *ACS Nano* 2014, 8, 4975-4983.
38. Piao, J.-G.; Wang, L.; Gao, F.; You, Y.-Z.; Xiong, Y.; Yang, L. *ACS Nano* 2014, 8, 10414-10425.

The invention claimed is:

1. A nanoparticle comprising:
   a) an inner core comprising a non-cellular material; and
   b) an outer surface comprising a bacterial membrane,
   wherein said bacterial membrane is a modified or processed bacterial membrane, or said bacterial membrane is derived from a bacteria outer membrane vesicle, or said nanoparticle is configured as a vaccine, and
   wherein said bacterial membrane in said outer surface has a protein loading yield, defined as the weight ratio of immobilized proteins to said nanoparticle, of at least from about 1 wt % to about 95 wt % or more.

2. The nanoparticle of claim 1, wherein the inner core supports the outer surface of the nanoparticle.

3. The nanoparticle of claim 1, wherein the bacterial membrane is a modified or processed bacterial membrane.

4. The nanoparticle of claim 1, wherein the cellular membrane comprises membrane-bound proteins, glycans and/or a complex lipopoly saccharide (LPS), or LPS comprising or consisting of lipid A, core polysaccharide, and O antigen.

5. The composition of claim 1, wherein the nanoparticle has a diameter from about 10 nm to about 10 um.

6. The nanoparticle of claim 1, which substantially lacks constituents of the bacterial cell or bacterial outer membrane vesicle from which the cellular membrane is derived.

7. The nanoparticle of claim 1, which substantially maintains natural structural integrity or activity of the cellular membrane or the constituents of the cellular membrane.

8. The nanoparticle of claim 1, which is biocompatible or biodegradable.

9. The nanoparticle of claim 1, which further comprises a releasable cargo.

10. The nanoparticle of claim 1, which is substantially stable, not aggregating, in a biological or physiological solution or environment, or biological buffer or in vivo environment.

11. The nanoparticle of claim 1, which substantially maintains its size in a biological or physiological solution or environment, or biological buffer or in vivo environment, for at least 1 hour.

12. The nanoparticle of claim 1, which is configured to elicit an immune response to the constituents of the bacterial membrane, or the bacterial membrane in the outer surface, or to the bacterium from which the bacterial membrane in the outer surface is derived.

13. A medicament delivery system, which comprises an effective amount of a nanoparticle comprising:
   a) an inner core comprising a non-cellular material; and
   b) an outer surface comprising a bacterial membrane,
   wherein said bacterial membrane is a modified or processed bacterial membrane, or said bacterial membrane is derived from a bacteria outer membrane vesicle, or said nanoparticle is configured as a vaccine, and
   wherein said bacterial membrane in said outer surface has a protein loading yield, defined as the weight ratio of immobilized proteins to said nanoparticle, of at least from about 1 wt % to about 95 wt % or more.

14. A pharmaceutical composition, which pharmaceutical composition comprises an effective amount of the nanoparticle of claim 1 and a pharmaceutically acceptable carrier or excipient.

15. A bacterial specific immunogenic composition, which immunogenic composition comprises an effective amount of a nanoparticle comprising:
   a) an inner core comprising a non-cellular material; and
   b) an outer surface comprising a bacterial membrane,
   wherein said bacterial membrane is a modified or processed bacterial membrane, or said bacterial membrane is derived from a bacteria outer membrane vesicle, or said nanoparticle is configured as a vaccine, and
   wherein said bacterial membrane in said outer surface has a protein loading yield, defined as the weight ratio of immobilized proteins to said nanoparticle, of at least from about 1 wt % to about 95 wt % or more.

16. A vaccine, which comprises an immunogenic composition, said immunogenic composition comprises an effective amount of a nanoparticle comprising:
   a) an inner core comprising a non-cellular material; and
   b) an outer surface comprising a bacterial membrane,
   wherein said bacterial membrane is a modified or processed bacterial membrane, or said bacterial membrane is derived from a bacteria outer membrane vesicle, or said nanoparticle is configured as a vaccine, and
   wherein said bacterial membrane in said outer surface has a protein loading yield, defined as the weight ratio of immobilized proteins to said nanoparticle, of at least from about 1 wt % to about 95 wt % or more.

\* \* \* \* \*